US010260062B2

(12) United States Patent
Ainley et al.

(10) Patent No.: US 10,260,062 B2
(45) Date of Patent: Apr. 16, 2019

(54) TARGETED GENOMIC ALTERATION

(75) Inventors: William M. Ainley, Carmel, IN (US); Michael G. Murray, Carmel, IN (US); Fyodor Urnov, Richmond, CA (US); Bryan Zeitler, Richmond, CA (US)

(73) Assignees: Sangamo Therapeutics, Inc., Richmond, CA (US); Dow AgroSciences LLC, Indianapolis, IN (US)

( * ) Notice: Subject to any disclaimer, the term of this patent is extended or adjusted under 35 U.S.C. 154(b) by 640 days.

(21) Appl. No.: 12/931,096

(22) Filed: Jan. 24, 2011

(65) Prior Publication Data

US 2011/0189775 A1 Aug. 4, 2011

Related U.S. Application Data

(60) Provisional application No. 61/336,457, filed on Jan. 22, 2010.

(51) Int. Cl.
*C12N 15/82* (2006.01)
*C12N 9/22* (2006.01)
*C12N 15/10* (2006.01)
*A01H 1/06* (2006.01)
*C12N 15/85* (2006.01)
*C12N 15/90* (2006.01)

(52) U.S. Cl.
CPC .............. *C12N 15/10* (2013.01); *A01H 1/06* (2013.01); *C12N 9/22* (2013.01); *C12N 15/8213* (2013.01); *C12N 15/85* (2013.01); *C12N 15/90* (2013.01); *C07K 2319/81* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox et al. | |
| 6,599,692 B1 | 7/2003 | Case et al. | |
| 6,607,882 B1 | 8/2003 | Cox et al. | |
| 6,689,558 B2 | 2/2004 | Case | |
| 6,824,978 B1 | 11/2004 | Cox et al. | |
| 6,933,113 B2 | 8/2005 | Case et al. | |
| 6,979,539 B2 | 12/2005 | Cox et al. | |
| 7,013,219 B2 | 3/2006 | Case et al. | |
| 7,102,055 B1* | 9/2006 | Baszczynski et al. | ........ 800/278 |
| 7,163,824 B2 | 1/2007 | Cox et al. | |
| 7,736,886 B2 | 6/2010 | Puchta et al. | |
| 7,838,733 B2 | 11/2010 | Wright et al. | |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2006/0188987 A1 | 8/2006 | Guschan et al. | |
| 2006/0195937 A1 | 8/2006 | Baszczynski | |
| 2007/0134796 A1 | 6/2007 | Holmes et al. | |
| 2008/0131962 A1 | 6/2008 | Miller | |
| 2008/0159996 A1 | 7/2008 | Ando et al. | |
| 2008/0182332 A1* | 7/2008 | Cai et al. | ...................... 435/468 |
| 2008/0299580 A1 | 12/2008 | DeKelver et al. | |
| 2009/0104700 A1 | 4/2009 | Samuel et al. | |
| 2009/0111119 A1 | 4/2009 | Doyon et al. | |
| 2009/0117617 A1 | 5/2009 | Holmes et al. | |
| 2009/0205083 A1 | 9/2009 | Gupta et al. | |
| 2009/0263900 A1 | 10/2009 | DeKelver et al. | |
| 2010/0199389 A1 | 8/2010 | Butler et al. | |
| 2011/0189775 A1 | 8/2011 | Ainley et al. | |
| 2011/0191877 A1 | 8/2011 | Russell et al. | |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |

(Continued)

OTHER PUBLICATIONS

Shukla et al 2009 Nature 459: p. 437-441. The reference is already of record.*
Cai et al 2009 Plant Molecular Biology 69: p. 699-709.*
Moeller et al 2008 (Bioscience 58:5 p. 391-401).*
Bitinate, et al., "Foki Dimerization is Required for DNA Cleavage," *PNAS USA* 95:10570-10575 (1998).
D'Halluin, et al., "Homologous Recombination: A Basis for Targeted Genome Optimization in Crop Species Such as *Maize*," *Plant Biotechnology J.* 6:93-102 (2008).
Doyon, et al., "Enhancing Zinc-Finger-Nuclease Activity with Improved Obligate Heterodimeric Architectures," *Nature Methods* 8:74-79 (2011).

(Continued)

*Primary Examiner* — Matthew R Keogh
(74) *Attorney, Agent, or Firm* — Pasternak Patent Law

(57) ABSTRACT

Disclosed herein are methods and compositions for targeted integration and/or targeted excision of one or more sequences into a cell, for example, for expression of one or more polypeptides of interest.

17 Claims, 15 Drawing Sheets

Specification includes a Sequence Listing.

(56) References Cited

FOREIGN PATENT DOCUMENTS

| WO | WO 98/53059 A1 | 11/1998 |
|---|---|---|
| WO | WO 98/53060 A1 | 11/1998 |
| WO | WO 98/54311 A1 | 12/1998 |
| WO | WO 00/27878 A1 | 5/2000 |
| WO | WO 01/53480 A1 | 7/2001 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 05/084190 A2 | 9/2005 |
| WO | WO 07/014275 A2 | 1/2007 |
| WO | 2007014181 A2 | 2/2007 |
| WO | WO 07/139898 A2 | 6/2007 |
| WO | WO 08/021207 A2 | 2/2008 |
| WO | 2008060510 A2 | 5/2008 |
| WO | 2008076290 A2 | 6/2008 |
| WO | 2009042163 A | 4/2009 |
| WO | WO 10/077319 A1 | 7/2010 |

OTHER PUBLICATIONS

Durai, et al., "Zinc Finger Nucleases: Custom-Designed Molecular Scissors for Genome Engineering of Plant and Mammalian Cells," *NAR* 33:5978-5990 (2005).

Hammerschmidt, et al., "Strategies to Perturb Zebrafish Development," *Methods Cell Biol* 59:87-115 (1999).

Kim, et al., "Chimeric Restriction Endonuclease," *PNAS USA* 91:883-887 (1994).

Kim, et al., "Insertion and Deletion Mutants of FOKI Restriction Endonuclease," *J. Biol. Chem.* 269:31978-31982 (1994).

Klee, et al., "Agrobacterium-Mediated Plant Transformation and Its Further Applications to Plant Biology," *Ann Rev of Plant Phys* 38:467-486 (1987).

Li, et al., "Functional Domains in FOK I Restriction Endonuclease," *PNAS USA* 89:4275-4279 (1992).

Li, et aL, "Alteration of the Cleavage Distance of FOK I Restriction Endonuclease by Insertion Mutagenesis," *PNAS USA* 90:2764-2768 (1993).

Miller, et al., "Repetitive Zinc-Binding Domains in the Protein Transcription Factor IIIA From Xenopus Oocytes,"*EMBO J.* 4:1609-1614 (1985).

Miller, et al., "An Improved Zinc-Finger Nuclease Architecture for Highly Specific Genome Editing," *Nat Biotechnology* 25:778-785 (2007).

Moehle, et al., "Targeted Gene Addition Into a Specified Location in the Human Genome Using Designed Zinc Finger Nucleases," *PNAS USA* 104:3055-3060 (2007).

Moore, et al., "Design of Polyzinc Finger Peptides with Structured Linkers," *PNAS USA* 98:1432-1436 (2001).

Moore, et al., "Improved DNA Binding Specificity From Polyzinc Finger Peptides by Using Strings of Two-Finger Units," *PNAS USA* 98:1437-1441 (2001).

Rhodes, et al., "Zinc Fingers: They Play a Key Part in Regulating the Activity of Genes in Many Species, From Yeast to Humans. Fewer Than 10 Years Ago No on Knew They Existed." *Scientific American* 268:56-65 (1993).

Shukla, et al., "Precise Genome Modification in the Crop Species *Zea Mays* Using Zinc-Finger Nucleases," *Nature* 459:437-441 (2009) with Supplementary on-line material.

Terada, et al., "Efficient Gene Targeting by Homologous Recombination in Rice," *Nat Biotechnology* 20:1030-1034 (2002).

Terada, et al., "Gene Targeting by Homologous Recombination as a Biotechnological Tool for Rice Functional Genomics," *Plant Physiol* 144:846-856 (2007).

Urnov, F.D., et al., "Genome Editing with Engineered Zinc Finger Nucleases," *Nat Rev Genet* 11:636-646 (2010).

Cai, et al., "Zinc Finger Nuclease-Mediated Gene Targeting in Plants," Induced Plant Mutations in the Genomics Era, pp. 223-226, Food and Agriculture of the United Nations, Rome (2009).

Maeder, M. L. et al., "Rapid "Open-Source" Engineering of Customized Zincfinger Nucleases for Highly Efficient Gene Modification," Mol. Cell 31:294-301 (2008).

\* cited by examiner

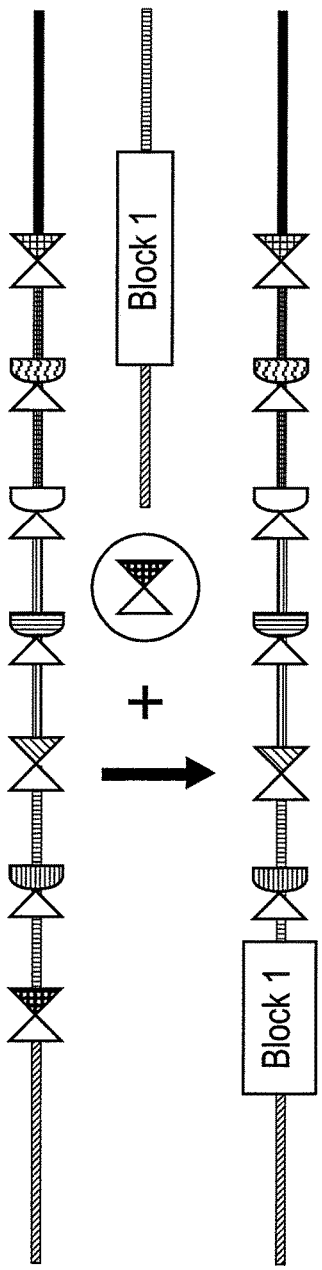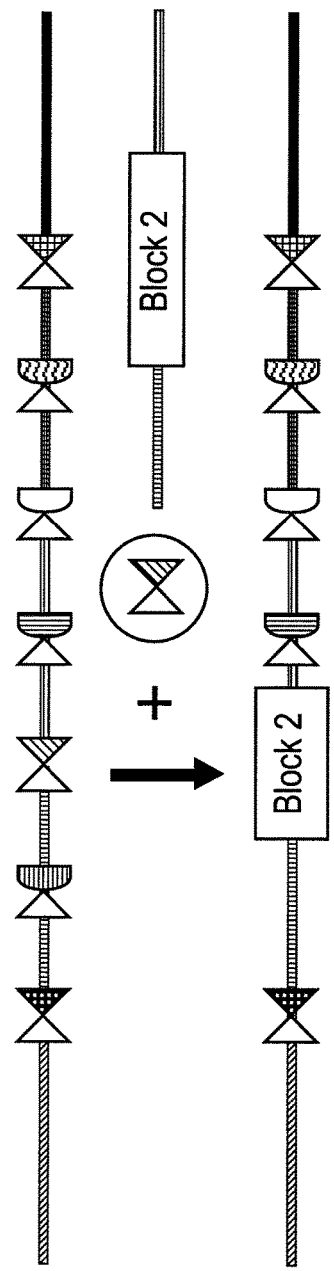

SEQUENCE LISTING

<160> NUMBER OF SEQ ID NOS: 75

<210> SEQ ID NO 1

```
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gccttttgca gtttatccac tagggacagg attg                              34

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aagactcccg cccatctctc tatgcccggg acaagtg                           37

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccaccccaca gtggggcctc tatgcccggg acaagtg                           37

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gagtccatgc tcaacaccgt gcactaggga caggattg                          38

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gccttttgca gtttatctct agaaagactg gagttgcaga                        40

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aagactcccg cccatccagg atgaggatga cca                               33

<210> SEQ ID NO 7
<211> LENGTH: 36
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 gcctttgca gtttatctct atgcccggga caagtg                                    36

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aagactcccg cccatctcac tagggacagg attg                                     34

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gagtccatgc tcaacaccgt gctagaaaga ctggagttgc aga                           43

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccaccccaca gtggggccta gaaagactgg agttgcaga                                39

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ccaccccaca gtggggcagg atgaggatga cca                                      33

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gagtccatgc tcaacaccgt gcaggatgag gatgacca                                 38

<210> SEQ ID NO 13
<211> LENGTH: 46
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 13
tctgcaactc cagtctttct agatctagaa agactggagt tgcaga          46

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aagactcccg cccatctaga tgggcgggag tctt                       34

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cacttgtccc gggcatagag ctctatgccc gggacaagtg                 40

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gagtccatgc tcaacaccgt gcacggtgtt gagcatggac tc              42

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tggtcatcct catcctcagg atgaggatga cca                        33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 gcctttttgca gtttatgata aactgcaaaa ggc                       33

<210> SEQ ID NO 19
<211> LENGTH: 34
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 19
caatcctgtc cctagtgcac tagggacagg attg                                   34

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccaccccaca gtggggcgcc ccactgtggg gtgg                                   34

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acaagagtgg attgatgatc tagagaggt                                         29

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctttgatgcc tatgtgacac gtaaacagt                                         29

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
ggtgttgtgg ctggtattgc ttacgctgg                                         29

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tactatgact tgatgttgtg tggtgactga                                        30

<210> SEQ ID NO 25
<211> LENGTH: 28
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 25
gagcggtcta aattccgacc cttatttc                                       28

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
aaacgatggc aggagtgccc tttttctatc aat                                 33

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcagtgcatg ttatgagc                                                  18

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
caggacataa atgaactgaa tc                                             22

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggcacagagt aagaggaaaa                                                20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agggacccag gtatacattt                                                20

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
cattccgccc ttgccagc                                              18

<210> SEQ ID NO 32

<400> SEQUENCE: 32

000

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gacaatgcct gactcccg                                              18

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
caaggaatga atgaaaccg                                             19

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ctgcaggaga caggtgcc                                              18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caatccccac ccaacact                                              18

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cctggggagt agcagtgtt                                             19

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gcagtgctct gtggggtc					18

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
cctggacagt tgtcaaaatt					20

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
gtgaacttat tatccatctg tcc				23

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
cactcagaca ccagggttt					19

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
agccgggaga tgaggaag					18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
cctgggctgc ttcacaac					18

<210> SEQ ID NO 44

<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aggagggtga tggtgagg                                                    18

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tgtgattact accctgccc                                                   19

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Arg Ser Asn Leu Ser Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ser Asp Ala Leu Thr Gln
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Ser Gly Asn Leu Thr Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Ser Gly Ser Leu Thr Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Ser Gly His Leu Ser Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ser Ala Asn Leu Ser Val
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Arg Ala Asn Leu Ser Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Ser Asp Asn Leu Arg Glu
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Arg Gly Thr Leu Ala Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 55

Thr Ser Ser Asn Arg Lys Thr
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Arg Ser Ala Arg Thr Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Ser Gly His Leu Ser Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ser Asp Asp Leu Ser Lys
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Asn Asp His Arg Lys Asn
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Ser Gly Asp Leu Thr Arg
1               5

<210> SEQ ID NO 61
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Ser Gly Ser Leu Thr Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ser Gly His Leu Ala Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Ser Ser Asp Leu Thr Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ser Asp Asn Leu Ser Glu
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Asn Ala His Arg Lys Thr
1               5

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
acggtgttga gcatggactc gtagaaga                                         28
```

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tctatgcccg ggacaagtgg ctggtgag                                         28

<210> SEQ ID NO 68
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gatgggcggg agtcttctgg gcaggctt                                         28

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ctagaaagac tggagttgca gatcacga                                         28

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Gln Pro Ala Thr Ser
1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Gln Pro Ala Thr Ala
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Thr Gln Pro Ala Thr Phe Gln
1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Thr Gln Pro Ala Leu Ser
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Gln Pro Ala Leu Ala
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Thr Gln Pro Ala Leu Phe Gln
1               5
```

TARGETED GENOMIC ALTERATION

CROSS-REFERENCE TO RELATED APPLICATIONS

This application claims the benefit of U.S. Provisional Application No. 61/336,457, filed Jan. 22, 2010, the disclosure of which is hereby incorporated by reference in its entirety.

STATEMENT OF RIGHTS TO INVENTIONS MADE UNDER FEDERALLY SPONSORED RESEARCH

Not applicable.

TECHNICAL FIELD

The present disclosure is in the field of genomic engineering, particularly targeted integration and/or targeted excision of one or more exogenous sequences into the genome of a cell.

BACKGROUND

Biotechnology has emerged as an essential tool in efforts to meet the challenge of increasing global demand for food production. Conventional approaches to improving agricultural productivity, e.g. enhanced yield or engineered pest resistance, rely on either mutation breeding or introduction of novel genes into the genomes of crop species by transformation. Both processes are inherently nonspecific and relatively inefficient. For example, conventional plant transformation methods deliver exogenous DNA that integrates into the genome at random locations. Thus, in order to identify and isolate transgenic lines with desirable attributes, it is necessary to generate thousands of unique random-integration events and subsequently screen for the desired individuals. As a result, conventional plant trait engineering is a laborious, time-consuming, and unpredictable undertaking. Furthermore the random nature of these integrations makes it difficult to predict whether pleiotropic effects due to unintended genome disruption have occurred. As a result, the generation, isolation and characterization of plant lines with engineered genes or traits has been an-extremely labor and cost-intensive process with a low probability of success.

Targeted gene modification overcomes the logistical challenges of conventional practices in plant systems, and as such has been a long-standing but elusive goal in both basic plant biology research and agricultural biotechnology. However, with the exception of "gene targeting" via positive-negative drug selection in rice or the use of pre-engineered restriction sites, targeted genome modification in all plant species, both model and crop, has until recently proven very difficult. Terada et al. (2002) *Nat Biotechnol* 20(10):1030; Terada et al. (2007) *Plant Physiol* 144(2):846; D'Halluin et al. (2008) *Plant Biotechnology. J.* 6(1):93.

In mammalian cells, stable transgenesis and targeted gene insertion have many potential applications in both gene therapy and cell engineering. However, current strategies are often inefficient and non-specifically insert the transgene into genomic DNA. The inability to control the location of genome insertion can lead to highly variable levels of transgene expression throughout the population due to position effects within the genome. Additionally, current methods of stable transgenesis and amplification of transgenes often result in physical loss of the transgene, transgene silencing over time, insertional mutagenesis by the integration of a gene and autonomous promoter inside or adjacent to an endogenous gene, the creation of chromosomal abnormalities and expression of rearranged gene products (comprised of endogenous genes, the inserted transgene, or both), and/or the creation of vector-related toxicities or immunogenicity in vivo from vector-derived genes that are expressed permanently due to the need for long-term persistence of the vector to provide stable transgene expression.

Recently, methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, United States Patent Publications 20030232410; 20050208489; 20050026157; 20050064474; and 20060188987, and International Publication WO 2007/014275, the disclosures of which are incorporated by reference in their entireties for all purposes. U.S. Patent Publication No. 20080182332 describes use of non-canonical zinc finger nucleases (ZFNs) for targeted modification of plant genomes and U.S. Patent Publication No. 20090205083 describes ZFN-mediated targeted modification of a plant EPSPS locus. In addition, Moehle et al. (2007) *Proc. Natl. Acad, Sci. USA* 104(9): 3055-3060) describe using designed ZFNs for targeted gene addition at a specified locus.

However, there remain needs for compositions and methods for targeted integration, including for targeted integration into plants for establishing stable, heritable genetic modifications in the plant and its progeny, and for target integration into mammalian cells for gene therapy and cell line development purposes.

SUMMARY

The present disclosure provides methods and compositions for expressing one or more products of an exogenous nucleic acid sequence (i.e. a protein or a RNA molecule) that has been integrated into a multiple insertion site integrated into a cell genome. The cell can be a eukaryotic cell, for example a plant, yeast or mammalian cell.

Integration of exogenous nucleic acid sequences is facilitated by genomic integration of a polynucleotide sequence comprising multiple target sites for one or more nucleases, for example zinc finger nucleases (ZFNs) into the cell's genome. The polynucleotides (also referred to herein as a multiple insertion site) allows for specific, targeted double-strand cleavage within the cell's genome, which double-stranded cleavage in turn results in integration of the exogenous sequence(s) through both homology-dependent and homology-independent mechanisms.

Thus, in one aspect, disclosed herein are nucleic acid molecules, also known as multiple insertion sites, comprising one or more target sites for nucleases such as zinc finger nucleases (ZFNs). In certain embodiments, the target sites are not present in the endogenous genome into which the multiple insertion site is integrated. The multiple insertion site may include one, two, three, four, five, six, seven or more target sites for nucleases. In certain embodiments, dimerization of the cleavage-half domains of two binding DNA-binding proteins that bind to adjacent target sites (paired target sites) is required for cleavage (e.g., a pair of nucleases, one binding to each site, is required for cleavage). In any of the multiple insertion sites described herein, one target site of each pair of target sites may comprise the same sequence. See, e.g., FIG. 1. In certain embodiments, the target sites of at least one pair are the same. In other embodiments, at least one pair of target sites comprises individual target sequences from different targets (e.g., different genes and/or genes from different organisms). In certain embodiments, at least one of the paired target sites comprise a sequence selected from the group consisting of SEQ ID NOs: 1-20. In certain embodiments, the multiple insertion site may include one more coding sequences, for example a plant transcription unit (PTU) comprising a phosphinothricin acetyl transferase (PAT) coding sequence, or a screening marker for use with mammalian cells.

The multiple insertion sites are integrated into the genome of a cell (e.g., plant or mammalian cell) to provide genomic targets for the nucleases (e.g., ZFNs). In certain embodiments, the target sites are situated such that one or more pairs of the zinc finger nucleases bind and cleave as homodimers. In other embodiments, the target sites are situated such that one or more pairs of the zinc finger nucleases bind and cleave as heterodimers.

In another aspect, disclosed herein are plants or seeds comprising one or more multiple insertion sites as described herein and/or one or more exogenous sequences integrated into the multiple insertion site. In certain embodiments, the multiple insertion site and/or exogenous sequence(s) is(are) integrated into the gametophyte of a maize plant.

In certain aspects, provided herein are modified mammalian cell lines, modified primary cells, modified stem cells and/or transgenic animals comprising one or more multiple insertion sites as described herein and/or one or more exogenous sequences integrated into the multiple insertion site.

In another aspect, provided herein is a method for integrating an exogenous sequence into the multiple insertion site integrated into the genome of a cell (e.g., plant or mammalian cell), the method comprising: (a) integrating a multiple insertion site polynucleotide comprising one or more target sites for nucleases into the genome of the cell; (b) providing and/or expressing one or more nucleases that bind to a first target site in the multiple insertion site polynucleotide, such that binding of the nuclease(s) to their target sites cleaves the genome of the cell; and (c) contacting the cell with a polynucleotide comprising an exogenous nucleic acid sequence, thereby resulting in homology dependent integration of the exogenous sequence into the genome of the cell within the multiple insertion site polynucleotide.

In another aspect, provided herein is a method for integrating multiple exogenous sequences into the genome of a cell (e.g., a plant or mammalian cell), the method comprising: (a) integrating a first multiple insertion site polynucleotide comprising one or more target sites for nucleases into the genome of the cell, wherein the first multiple insertion site polynucleotide comprises at least one first gene flanked by target sites for first and second nucleases; and (b) expressing the first or second nuclease in the cell in the presence of a second multiple insertion site polynucleotide comprising at least one second gene flanked by target sites for third and fourth nucleases, thereby resulting in integration of the first and second genes into the genome of the cell. In certain embodiments, the method further comprises repeating, one or more times, the step of expressing the appropriate nucleases present on the inserted multiple insertion sites to integrate additional exogenous sequences, including coding sequences and/or nuclease sites. The nucleases may be heterodimeric ZFNs and there may be one monomer in common as between one or more of the nucleases. In some embodiments, the exogenous DNA sequence for insertion may comprise a ZFN half target site such that upon integration of the exogenous sequence, a novel ZFN target site is created comprising the half target site associated with the donor DNA, and a half target site associated with the genomic DNA. This novel ZFN target site can serve as a target site for a similarly novel heterodimeric ZFN.

In another aspect, disclosed herein is a method for expressing the product of one or more exogenous nucleic acid sequences in a cell (e.g., plant or mammalian cell), the method comprising: integrating one or more exogenous nucleic acid sequences according to any of the methods described herein, such that the exogenous sequence is integrated into the genome of the cell in the integrated nucleic acid molecule and the product of the exogenous sequence is expressed.

Also provided is a method of deleting one or more genes inserted into the genome of a cell, the method comprising, integrating a plurality of exogenous sequences by any of the methods described herein and expressing the appropriate nucleases in the cell such that one or more of the exogenous sequences are deleted from the genome. In certain embodiments, the exogenous sequences deleted are marker genes. In certain embodiments, the deletion of the exogenous sequence and the subsequent re-joining of the ends within the genome creates a functional gene or sequence in the genomic location, e.g. the creation of an expressible screening marker.

In yet another aspect, a method of providing a genomically altered cell is provided, the method comprising integrating and/or excising one or more exogenous nucleic acid sequences in a first cell according to any of the methods described herein, allowing the first cell to develop into a first sexually mature organism, crossing the organism with a second organism comprising genomic alterations at an allelic position to generate a second cell with the genomic alterations of first and second organisms. In certain embodiments, the organism(s) is(are) plants. In other embodiments, the organism(s) is/are transgenic animals.

In any of the methods described herein, the methods may be used in combination with other methods of genomic alteration, including targeted integration and/or targeted inactivation at one or more endogenous loci. Furthermore, in any of the methods described herein, the nuclease may comprise one or more fusion proteins comprising a zinc finger binding domain and a cleavage half-domain, wherein the zinc finger binding domain has been engineered to bind to a target site in the multiple insertion site. Furthermore, in any of these methods, the exogenous nucleic acid sequence comprises one or more sequences that is (are) homologous to the sequences in multiple insertion site and/or endogenous sequences in the region where the multiple insertion site is integrated.

In any of the methods described herein, the one or more multiple insertion sites may be integrated into the genome by any suitable method, for example, by targeted integration via a nuclease (e.g., ZFN) using ZFNs that target the endogenous gene into which insertion is desired. Alternatively, the one or more multiple insertion sites may be randomly integrated into the cell's genome, using standard techniques.

The exogenous nucleic acid sequence may comprise a sequence, encoding one or more functional polypeptides (e.g., a cDNA), with or without one or more promoters and/or may produce one or more RNA sequences (e.g., via one or more shRNA expression cassettes), which impart desirable traits to the organism. Such traits in plants include, but are not limited to, herbicide resistance or tolerance;

insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch quantity and quality; oil quantity and quality; protein quality and quantity; amino acid composition; and the like. Of course, any two or more exogenous nucleic acids of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired. In certain embodiments, the exogenous nucleic acid sequence comprises a sequence encoding a herbicide resistance protein (e.g., the AAD (aryloxyalkanoate dioxygenase) gene) and/or functional fragments thereof. Expression of the integrated sequence can be driven by a promoter operably linked to the integrated sequence. Alternatively, the integrated sequence is promotorless and transcription is driven by the endogenous promoter in the region of insertion of the multiple insertion site polynucleotide. In other embodiments, the cleavage and imprecise repair of a binding site may inactivate or activate genes of interest. In certain embodiments, the polynucleotide is a plasmid. In other embodiments, the polynucleotide is a linear DNA molecule.

In mammalian cells, the methods and compositions of the invention may be used for cell line construction, e.g. for the construction of cell lines expressing multimeric polypeptides such as antibodies. In some embodiments, the cell lines may be used for research purposes, e.g. for the construction of cell lines expressing members of a pathway of interest. In some embodiments, primary cells or stem cells may be used to express multimeric proteins of interest for cell therapeutic purposes.

In another aspect, provided herein are methods of measuring zinc finger nuclease activity. In certain embodiments, the methods comprise: (a) providing at least one zinc finger nuclease and a nucleic acid molecule as described herein, wherein each of the paired target sites comprises two zinc finger nuclease half target sites to which the zinc finger nuclease binds, and a cut site that is cut by the bound zinc finger nuclease, which cut site is interposed between the half target sites; (b) combining the zinc finger nuclease with the nucleic acid such that the zinc finger nuclease cleaves the paired target site at least within the cut site; (c) sequencing at least the cut site to generate sequence data; and (d) comparing in the sequence data the number and length of base pair deletions within the cut site to the number and length of base pair deletions within the cut site in the absence of the zinc finger nuclease, to thereby measure the zinc finger nuclease activity at the paired target sites. In certain embodiments, a deletion of more than one base pair indicates increased activity of the zinc finger nuclease(s).

In yet other embodiments, provided herein are methods for optimizing zinc finger nuclease activity at a paired target site. In certain embodiments, the methods comprise (a) providing at least one zinc finger nuclease and a nucleic acid molecule as described herein, wherein each of the paired target sites comprises two zinc finger nuclease half target sites to which the zinc finger nucleast binds, and a cut site that is cut by the bound zinc finger nuclease, which cut site is interposed between the half target sites; (b) combining the one or more zinc finger nucleases with the nucleic acid such that the zinc finger nuclease cleaves the paired target site at least within the cut site; (c) determining the zinc finger nuclease activity level at the cut site; (d) varying the number of base pairs in the cut site; (e) repeating steps (b)-(d) a plurality of times; and (f) selecting the cut site for incorporation into the nucleic acid, which comprises the number of base pairs providing the highest level of zinc finger nuclease activity, thereby optimizing zinc finger nuclease activity at the paired target site.

In any of the methods described herein involving zinc finger nucleases, the first and second cleavage half-domains are from a Type IIS restriction endonuclease, for example, FokI or StsI. Furthermore, in any of the methods described herein, at least one of the fusion proteins may comprise an alteration in the amino acid sequence of the dimerization interface of the cleavage half-domain, for example such that obligate heterodimers of the cleavage half-domains are formed.

In any of the methods described herein, the plant cell can comprise a monocotyledonous or dicotyledonous plant cell. In certain embodiments, the plant cell is a crop plant, for example maize. In certain embodiments, the cell can comprise a mammalian cell such as a primary cell, a cell line, or a stem cell. In some embodiments, the mammalian cell line can be used for the production of polypeptides of interest.

BRIEF DESCRIPTION OF THE DRAWINGS

FIG. 1 is a schematic depicting exemplary multiple insertion site as described herein. FIG. 1 shows a multiple insertion site made up of 7 ZFN target sites. The ZFN pairs that bind to the target sites are depicted as geometric figures. "Block 1" is an exogenous sequence that is integrated into the multiple insertion site in the presence of the appropriate ZFN pair, while maintaining the ZFN target sites (shaded and checkered triangles). FIG. 1 shows integration of "Block 1" into a multiple insertion site in the presence of the appropriate ZFN pair in place of the ZFN target sites.

FIG. 2 is a schematic depicting the exemplary multiple insertion site as shown in FIG. 1 in which "Block 2" is an exogenous sequence that is integrated into the multiple insertion site in the presence of the appropriate ZFN pair.

DETAILED DESCRIPTION

Figure 3:
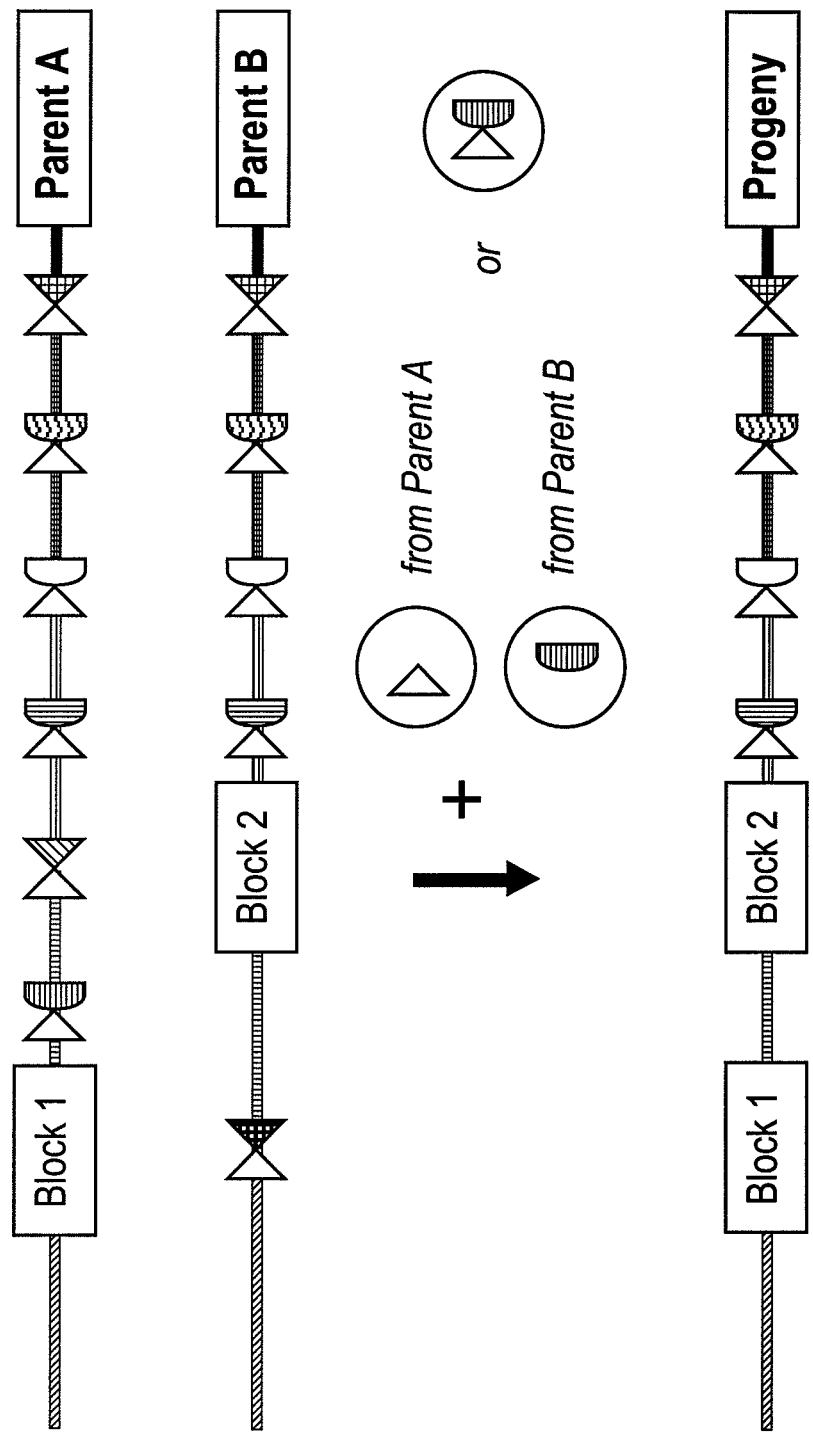
FIG. 3 is a schematic of inter-allelic recombination enhanced by ZFNs. Two inserts at an identical genomic location, but are displaced from each other, can undergo homologous recombination or strand exchange after double-stranded cleavage by a ZFN. The ZFN pair (with both ZFN monomers expressed together) can be provided by crossing a plant expressing the ZFN pair with plants comprising both alleles together or by introducing the two ZFN monomers from both sides of a cross with plants containing a single allele.

The present disclosure relates to methods and compositions for targeted integration (TI) into a genome, for example a crop plant such as maize or a mammalian cell. A multiple insertion site containing multiple target sites for one or more nucleases (e.g., ZFNs) is integrated into the genome. Following integration of the multiple insertion site into the genome, the appropriate nucleases are introduced into the cell along with an exogenous sequence to be inserted.

In certain embodiments, the nuclease(s) comprise one or more ZFNs. ZFNs typically comprise a cleavage domain (or a cleavage half-domain) and a zinc finger binding domain and may be introduced as proteins, as polynucleotides encoding these proteins or as combinations of polypeptides and polypeptide-encoding polynucleotides. Zinc finger nucleases typically function as dimeric proteins following dimerization of the cleavage half-domains. Obligate heterodimeric ZFNs, in which the ZFN monomers bind to the "left" and "right" recognition domains can associate to form an active nuclease have been described. See, e.g., U.S. Patent Publication No. 2008/0131962. Thus, given the appropriate target sites, a "left" monomer could form an active ZF nuclease with any "right" monomer. This significantly increases the number of useful nuclease sites based on proven left and right domains that can be used in various combinations. For example, recombining the binding sites of 4 homodimeric ZF nucleases yields an additional 12 heterodimeric ZF nucleases. More importantly, it enables a systematic approach to transgenic design such that every new introduced sequence becomes flanked with a unique ZFN site that can be used to excise the gene back out or to target additional genes next to it. Additionally, this method can simplify strategies of stacking into a single locus that is driven by ZFN-dependent double-strand breaks A zinc finger binding domain can be a canonical (C2H2) zinc finger or a non-canonical (e.g., C3H) zinc finger. Furthermore, the zinc finger binding domain can comprise one or more zinc fingers (e.g., 2, 3, 4, 5, 6, 7, 8, 9 or more zinc fingers), and can be engineered to bind to any sequence within the multiple insertion site. The presence of such a fusion protein (or proteins) in a cell results in binding of the fusion protein(s) to its (their) binding site(s) and cleavage within the multiple insertion site, which results in integration of the exogenous sequence(s).

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. Nos. 5,789,53.8; 5,925,523; 6,007,988; 6,013,453; 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. Suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach,* editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual,* Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach,* editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual,* Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence which, in conjunction with a second polypeptide (either identical or different) forms a complex having cleavage activity (preferably double-strand cleavage activity).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a coding sequence for any polypeptide or fragment thereof, a functioning version of a malfunctioning endogenous molecule or a malfunctioning version of a normally-functioning endogenous molecule. Additionally, an exogenous molecule can comprise a coding sequence from another species that is an ortholog of an endogenous gene in the host cell.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation:

"Modulation" of gene expression refers to a change in the activity of a gene. Modulation of expression can include, but is not limited to, gene activation and gene repression.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato; sunflower, cotton, sugarbeet, potato, lettuce, melon, soybean, canola (rapeseed), and alfalfa. Plant cells may be from any part of the plant and/or from any stage of plant development.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical: See, for example, Fields et al. (1989) *Nature* 340:245-246; U.S. Pat. No. 5,585,245 and PCT WO 98/44350.

Multiple Insertion Sites

Disclosed herein are multiple insertion sites, namely polynucleotides comprising a plurality of zinc finger nuclease (ZFN) binding sites such that, upon binding of the appropriate ZFN pair, the multiple insertion site is cleaved between the target sites of the ZFN pair.

The target sites included on the multiple insertion site preferably are not found in the genome of the cell into which it is integrated. As such, the occurrence of unwanted cleavage within the genome is reduced or eliminated. Any number of target sites can be included in the multiple insertion site polynucleotide, for example 1-50 (or any number therebetween), preferably between 2 and 30 (or any number therebetween, and even more preferably between 5 and 20 (or any number therebetween). For zinc finger nucleases the target sites are typically in pairs such that the zinc finger nucleases form homo- or hetero-dimers to cleave at the appropriate site.

Furthermore, as shown in FIG. 1, one target site of each pair of the target site (the shaded triangle FIG. 1) may be the same across the entire multiple insertion site. Alternatively, the heterodimeric pairs may be different as between sites.

The multiple insertion site may include targets sites bound by only homodimers, target sites bound by only heterodimers, or a combination of target sites bound by homo- and hetero-dimers. Target sites bound by homodimers may be preferred in some cases for one or more of the following reasons: delivery of one ZFN may be more efficient than two, homodimerization reduces the issue of unequal stoichiometry due to unequal expression of ZFNs; toxicity from cleavage at off-target sites may be reduced; the homodimer is half as likely to be disrupted by when using CCHC (non-canonical) zinc finger domains; and/or the total number of unique targetable sites can be expanded. Alternatively, heterodimers may be preferred in other cases since they allow for mixing and matching of different target sites, and thus a potential increase in targetable sites for ZFN pairs. Also, heterodimers may allow for sequential addition of donors as needed by the practioner. Heterodimeric combinations can also allow for the specific deletion of any desired sections of a donor through the use of novel ZFN pairs.

It will be apparent that is not necessary for a target site to be a multiple of three nucleotides for zinc finger nucleases. For example, in cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger, etc.

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. To provide but one example, a four-finger binding domain can bind to a 13-nucleotide target site comprising, in sequence, two contiguous 3-nucleotide subsites, an intervening nucleotide, and two contiguous triplet subsites.

Distance between sequences (e.g., target sites) refers to the number of nucleotides or nucleotide pairs intervening between two sequences, as measured from the edges of the sequences nearest each other.

In certain embodiments in which cleavage depends on the binding of two zinc finger domain/cleavage half-domain fusion molecules to separate target sites, the two target sites can be on opposite DNA strands. In other embodiments, both target sites are on the same DNA strand.

The multiple insertion site can be integrated anywhere in the plant genome. In certain embodiments, the multiple insertion site is integrated into a Zp15 in maize genome, which as described in U.S. application Ser. No. 12/653,735 is a desirable site for targeted integration of exogenous sequences.

DNA-Binding Domains

Any DNA-binding domain can be used in the methods disclosed herein. In certain embodiments, the DNA binding domain comprises a zinc finger protein. A zinc finger binding domain comprises one or more zinc fingers. Miller et al. (1985) *EMBO J.* 4:1609-1614; Rhodes (1993) *Scientific American* February :56-65; U.S. Pat. No. 6,453,242. The zinc finger binding domains described herein generally include 2, 3, 4, 5, 6 or even more zinc fingers.

Typically, a single zinc finger domain is about 30 amino acids in length. Structural studies have demonstrated that each zinc finger domain (motif) contains two beta sheets (held in a beta turn which contains the two invariant cysteine residues) and an alpha helix (containing the two invariant histidine residues), which are held in a particular conformation through coordination of a zinc atom by the two cysteines and the two histidines.

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and $C_4$ zinc fingers (those in which the zinc ion is coordinated by four cysteine residues). See also WO 02/057293 and also U.S. Patent Publication No. 20080182332 regarding non-canonical ZFPs for use in plants.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in co-owned WO 02/077227.

Since an individual zinc finger binds to a three-nucleotide (i.e., triplet) sequence (or a four-nucleotide sequence which can overlap, by one nucleotide, with the four-nucleotide binding site of an adjacent zinc finger), the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. As noted herein, binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain.

In a multi-finger zinc finger binding domain, adjacent zinc fingers can be separated by amino acid linker sequences of approximately 5 amino acids (so-called "canonical" inter-finger linkers) or, alternatively, by one or more non-canonical linkers. See, e.g., co-owned U.S. Pat. Nos. 6,453,242 and 6,534,261. For engineered zinc finger binding domains comprising more than three fingers, insertion of longer ("non-canonical") inter-finger linkers between certain of the zinc fingers may be desirable in some instances as it may increase the affinity and/or specificity of binding by the binding domain. See, for example, U.S. Pat. No. 6,479,626 and WO 01/53480. Accordingly, multi-finger zinc finger binding domains can also be characterized with respect to the presence and location of non-canonical inter-finger linkers. For example, a six-finger zinc finger binding domain comprising three fingers (joined by two canonical inter-finger linkers), a long linker and three additional fingers (joined by two canonical inter-finger linkers) is denoted a 2×3 configuration. Similarly, a binding domain comprising two fingers (with a canonical linker therebetween), a long linker and two additional fingers (joined by a canonical linker) is denoted a 2×2 configuration. A protein comprising three two-finger units (in each of which the two fingers are joined by a canonical linker), and in which each two-finger unit is joined to the adjacent two finger unit by a long linker, is referred to as a 3×2 configuration.

The presence of a long or non-canonical inter-finger linker between two adjacent zinc fingers in a multi-finger binding domain often allows the two fingers to bind to subsites which are not immediately contiguous in the target sequence. Accordingly, there can be gaps of one or more nucleotides between subsites in a target site; i.e., a target site can contain one or more nucleotides that are not contacted by a zinc finger. For example, a 2×2 zinc finger binding domain can bind to two six-nucleotide sequences separated by one nucleotide, i.e., it binds to a 13-nucleotide target site. See also Moore et al. (2001a) Proc. Natl. Acad. Sci. USA 98:1432-1436; Moore et al. (2001b) Proc. Natl. Acad. Sci. USA 98:1437-1441 and WO 01/53480.

As mentioned previously, a target subsite is a three- or four-nucleotide sequence that is bound by a single zinc finger. For certain purposes, a two-finger unit is denoted a "binding module." A binding module can be obtained by, for example, selecting for two adjacent fingers in the context of a multi-finger protein (generally three fingers) which bind a particular six-nucleotide target sequence. Alternatively, modules can be constructed by assembly of individual zinc fingers. See also WO 98/53057 and WO 01/53480.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, ISceIII, I-CreI, I-TevI, I-TevII and I-TevIII are known. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue. In addition, the DNA-binding specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication No. 20070117128.

As another alternative, the DNA-binding domain may be derived from a leucine zipper protein. Leucine zippers are a class of proteins that are involved in protein-protein interactions in many eukaryotic regulatory proteins that are important transcriptional factors associated with gene expression. The leucine zipper refers to a common structural motif shared in these transcriptional factors across several kingdoms including animals, plants, yeasts, etc. The leucine zipper is formed by two polypeptides (homodimer or heterodimer) that bind to specific DNA sequences in a manner where the leucine residues are evenly spaced through an α-helix, such that the leucine residues of the two polypeptides end up on the same face of the helix. The DNA binding specificity of leucine zippers can be utilized in the DNA-binding domains disclosed herein.

In some embodiments, the DNA binding domain is an engineered domain from a TAL effector derived from the plant pathogen Xanthomonas (see, Miller et al. (2010) Nature Biotechnology, December 22 [Epub ahead of print]; Boch et al, (2009) Science 29 Oct. 2009 (10.1126/science.117881) and Moscou and Bogdanove, (2009) Science 29 Oct. 2009 (10.1126/science.1178817).

Cleavage Domains

As noted above, the DNA-binding domain may be associated with a cleavage (nuclease) domain. For example, homing endonucleases may be modified in their DNA-binding specificity while retaining nuclease function. In addition, zinc finger proteins may also be fused to a cleavage domain to form a zinc finger nuclease (ZFN).

The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press,1993). Non limiting examples of homing endonucleases and meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue. One or more of these enzymes (or functional fragments thereof) can be used as a source of cleavage domains and cleavage half-domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI. This particular enzyme is active as a dimer. Bitinaite et al. (1998) Proc. Natl. Acad. Sci. USA 95: 10,570-10,575. Accordingly, for the purposes of the present disclosure, the portion of the FokI enzyme used in the disclosed fusion proteins is considered a cleavage half-domain. Thus, for targeted double-stranded cleavage, and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in co-owned International Publication WO 2007/014275, incorporated by reference herein in its entirety.

To enhance cleavage specificity, cleavage domains may also be modified. In certain embodiments, variants of the cleavage half-domain are employed these variants minimize or prevent homodimerization of the cleavage half-domains. Non-limiting examples of such modified cleavage half-domains are described in detail in WO 2007/014275, incorporated by reference in its entirety herein. See, also, Examples. In certain embodiments, the cleavage domain comprises an engineered cleavage half-domain (also referred to as dimerization domain mutants) that minimize or prevent homodimerization are known to those of skill the art and described for example in U.S. Patent Publication Nos. 20050064474 and 20060188987, incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains. See, e.g., U.S. Patent Publication Nos. 20050064474 and 20060188987; International Patent Publication WO 07/139898; Miller et al. (2007) *Nat. Biotechnol.* 25(7):778-785; and Doyon et al (2011) *Nature Methods* 8(1):74-79.

Additional engineered cleavage half-domains of FokI that form obligate heterodimers can also be used in the ZFNs described herein. In one embodiment, the first cleavage half-domain includes mutations at amino acid residues at positions 490 and 538 of FokI and the second cleavage half-domain includes mutations at amino acid residues 486 and 499.

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotides or more). In general, the point of cleavage lies between the target sites.

Fusion Proteins

Methods for design and construction of fusion proteins (and polynucleotides encoding same) are known to those of skill in the art. For example, methods for the design and construction of fusion proteins comprising DNA-binding domains (e.g., zinc finger domains) and regulatory or cleavage domains (or cleavage half-domains), and polynucleotides encoding such fusion proteins, are described in co-owned U.S. Pat. Nos. 6,453,242 and 6,534,261 and U.S. Patent Application Publications 2007/0134796 and 2005/0064474; herein incorporated by reference in their entireties. In certain embodiments, polynucleotides encoding the fusion proteins are constructed. These polynucleotides can be inserted into a vector and the vector can be introduced into a cell (see below for additional disclosure regarding vectors and methods for introducing polynucleotides into cells).

In certain embodiments of the methods described herein, a zinc finger nuclease comprises a fusion protein comprising a zinc finger binding domain and a cleavage half-domain from the FokI restriction enzyme, and two such fusion proteins are expressed in a cell. Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and a zinc finger binding domain. In this case, a single fusion protein is expressed in a cell and, without wishing to be bound by theory, is believed to cleave DNA as a result of formation of an intramolecular dimer of the cleavage half-domains.

In certain embodiments, the components of the fusion proteins (e.g., ZFP-FokI fusions) are arranged such that the zinc finger domain is nearest the amino terminus of the fusion protein, and the cleavage half-domain is nearest the carboxy-terminus. This mirrors the relative orientation of the cleavage domain in naturally-occurring dimerizing cleavage domains such as those derived from the FokI enzyme, in which the DNA-binding domain is nearest the amino terminus and the cleavage half-domain is nearest the carboxy terminus. In these embodiments, dimerization of the cleavage half-domains to form a functional nuclease is brought about by binding of the fusion proteins to sites on opposite DNA strands, with the 5' ends of the binding sites being proximal to each other.

In additional embodiments, the components of the fusion proteins (e.g., ZFP-FokI fusions) are arranged such that the cleavage half-domain is nearest the amino terminus of the fusion protein, and the zinc finger domain is nearest the carboxy-terminus. In these embodiments, dimerization of the cleavage half-domains to form a functional nuclease is brought about by binding of the fusion proteins to sites on opposite DNA strands, with the 3' ends of the binding sites being proximal to each other.

In yet additional embodiments, a first fusion protein contains the cleavage half-domain nearest the amino terminus of the fusion protein, and the zinc finger domain nearest the carboxy-terminus, and a second fusion protein is arranged such that the zinc finger domain is nearest the amino terminus of the fusion protein, and the cleavage half-domain is nearest the carboxy-terminus. In these embodiments, both fusion proteins bind to the same DNA strand, with the binding site of the first fusion protein containing the zinc finger domain nearest the carboxy terminus located to the 5' side of the binding site of the second fusion protein containing the zinc finger domain nearest the amino terminus.

In certain embodiments of the disclosed fusion proteins, the amino acid sequence between the zinc finger domain and the cleavage domain (or cleavage half-domain) is denoted the "ZC linker." The ZC linker is to be distinguished from the inter-finger linkers discussed above. See, e.g., U.S. Patent Publications 20050064474A1 and 20030232410, and International Patent Publication WO05/084190, for details on obtaining ZC linkers that optimize cleavage.

In one embodiment, the disclosure provides a ZFN comprising a zinc finger protein having one or more of the recognition helix amino acid sequences shown in Table 1. In another embodiment, provided herein is a ZFP expression vector comprising a nucleotide sequence encoding a ZFP having one or more recognition helices shown in Table 1.

Targeted Integration

The disclosed methods and compositions can be used to cleave DNA in any cell genome into which a multiple insertion site has been integrated, which facilitates the stable, targeted integration of an exogenous sequence into the multiple insertion site and/or excision of exogenous sequences in the presence of the appropriate ZFN pairs. See, FIGS. 1 and 2.

Also described herein are methods in which ZFN insertion sites, as part of an exogenous sequence, are introduced into the cell's genome in series. See, FIGS. 4 and 5. For example, an exogenous sequence flanked by different combination of heterodimeric nuclease sites is inserted in the genome. Subsequently a ZFN pair that cleaves at one of the appropriate flanking ZFN sites is introduced into the cell in the presence of another exogenous sequence, which again includes different combinations of heterodimeric nuclease sites. The process can be repeated as desired to insert exogenous sequences. In addition, in the presence of the appropriate ZFN pairs, one or more exogenous sequences may be excised from the genome.

Figure 6:
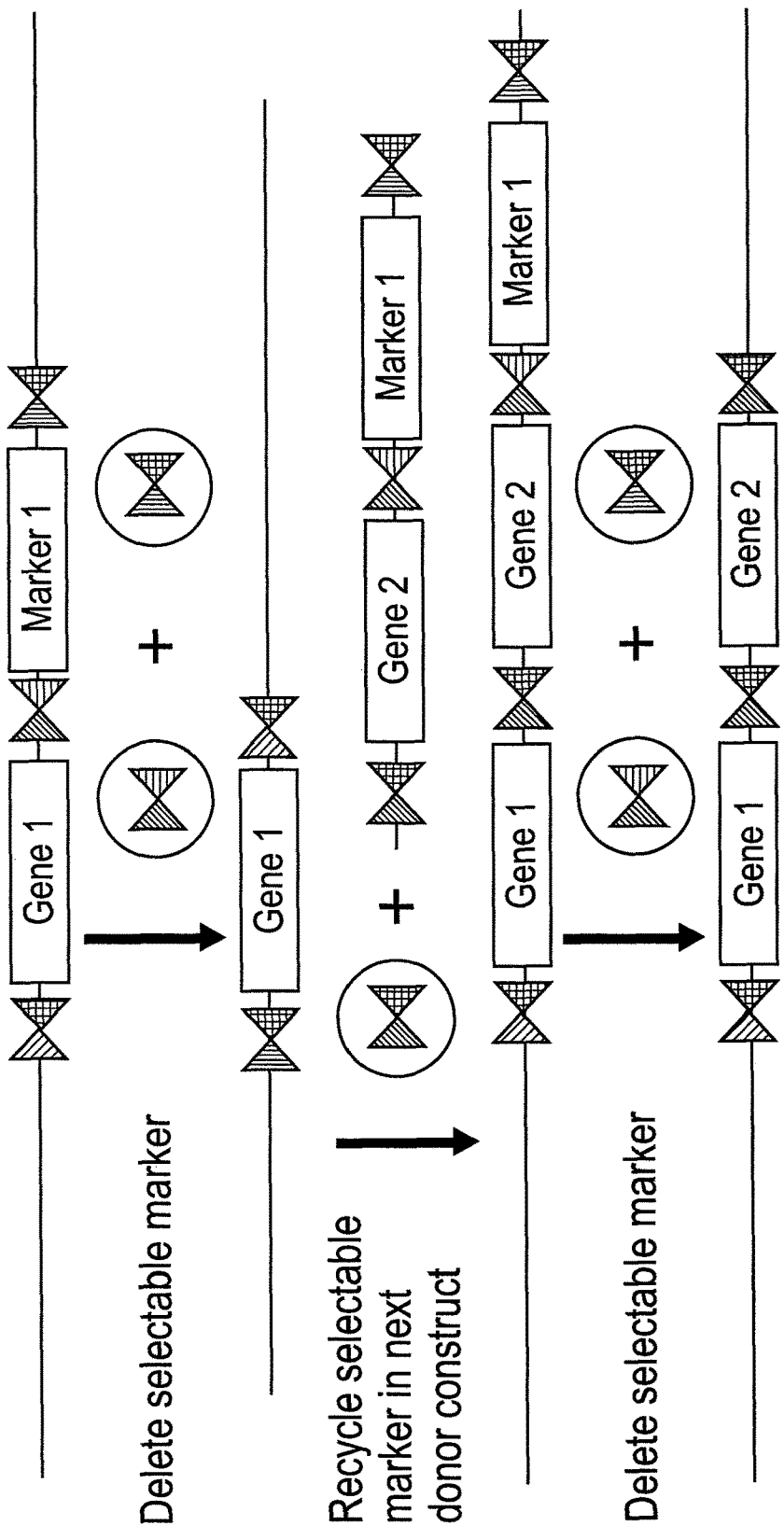
FIG. 6 is a schematic depicting excision and "recycling" of inserted marker genes using ZFNs heterodimers (depicted as triangles with different shadings).

FIG. 6 shows another embodiment in which the exogenous sequence comprises a marker gene and a gene of interest. Both the marker gene and gene of interest are flanked by different ZFN binding sites (depicted as triangles with different shadings), so that the marker gene can be deleted as appropriate, for example when inserting additional genes. In organisms such as plants where there are a limited number of effective selectable markers, this allows the use of as few as one selectable marker gene, greatly facilitating the potential to stack genes of interest. In certain embodiments, for example depending on efficiency of homology-directed DNA repair, a "split" selectable marker may be used. Correct integration of a donor DNA sequence using a split-selectable marker creates an expressible selectable marker gene. Selectable markers can be excised from an integrated DNA sequence and can therefore be recycled. In another embodiment, the exogenous sequence for removal is flanked in the genome by partial sequences of a split marker gene. Upon excision, the marker gene is re-constructed, resulting in the creation of a functional marker gene. Use of selectable marker excision limits the number of selectable markers needed to two or possibly only one.

For targeted integration into an integrated multiple insertion site as described herein, one or more DNA-binding domains (e.g., ZFPs) are engineered to bind a target site at or near the predetermined cleavage site, and a fusion protein comprising the engineered DNA-binding domain and a cleavage domain is expressed in a cell. Upon binding of the DNA-binding (e.g., zinc finger) portion of the fusion protein to the target site, the DNA is cleaved, preferably via a double-stranded break, near the target site by the cleavage domain.

The presence of a double-stranded break in the multiple insertion site facilitates integration of exogenous sequences via homologous recombination. In certain embodiments, the polynucleotide comprising the exogenous sequence to be inserted into the multiple insertion site will include one or more regions of homology with the multiple insertion site polynucleotide and/or the surrounding genome to facilitate homologous recombination. Approximately 25, 50, 100, 200, 500, 750, 1,000, 1,500, 2,000 nucleotides or more of sequence homology between a donor and a genomic sequence (or any integral value between 10 and 2,000 nucleotides, or more) Will support homologous recombination therebetween. In certain embodiments, the homology arms are less than 1,000 basepairs in length. In other embodiments, the homology arms are less than 750 basepairs in length. See, also, U.S. Provisional Patent Application No. 61/124,047, which is incorporated herein by reference. A donor molecule (exogenous sequence) can contain several, discontinuous regions of homology to cellular chromatin. For example, for targeted insertion of sequences not normally present in a region of interest, said sequences can be present in a donor nucleic acid molecule and flanked by regions of homology to a gene sequence in the region of interest.

Any sequence of interest (exogenous sequence) can be introduced into or excised from a multiple insertion site as described herein. Exemplary exogenous sequences include, but are not limited to any polypeptide coding sequence (e.g., cDNAs), promoter, enhancer and other regulatory sequences (e.g., interfering RNA sequences, snRNA expression cassettes, epitope tags, marker genes, cleavage enzyme recognition sites and various types of expression constructs. Such sequences can be readily obtained using standard molecular biological techniques (cloning, synthesis, etc.) and/or are commercially available. The exogenous sequence can be introduced into the cell prior to, concurrently with, or subsequent to, expression of the fusion protein(s).

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a nanoparticle, liposome or poloxamer, or can be delivered to plant cells by bacteria or viruses (e.g., *Agrobacterium, Rhizobium* sp. NGR234, *Sinorhizoboium meliloti, Mesorhizobium loti,* tobacco mosaic virus, potato virus X, cauliflower mosaic virus and cassava vein mosaic virus. See, e.g., Chung et al. (2006) *Trends Plant Sci.* 11(1):1-4.

As detailed above, the binding sites on the multiple insertion site for two fusion proteins (homodimers or heterodimers), each comprising a zinc finger binding domain and a cleavage half-domain, can be located 5-8 or 15-18 nucleotides apart, as measured from the edge of each binding site nearest the other binding site, and cleavage occurs between the binding sites. Whether cleavage occurs at a single site or at multiple sites between the binding sites is immaterial, since the cleaved genomic sequences are replaced by the donor sequences. Thus, for efficient alteration of the sequence of a single nucleotide pair by targeted recombination, the midpoint of the region between the binding sites is within 10,000 nucleotides of that nucleotide pair, preferably within 1,000 nucleotides, or 500 nucleotides, or 200 nucleotides, or 100 nucleotides, or 50 nucleotides, or 20 nucleotides, or 10 nucleotides, or 5 nucleotide, or 2 nucleotides, or one nucleotide, or at the nucleotide pair of interest.

Methods and compositions are also provided that may enhance levels of targeted recombination including, but not limited to, the use of additional ZFP-functional domain fusions to activate expression of genes involved in homologous recombination, such as, for example, plant genes of the RAD54 epistasis group (e.g., AtRad54, AtRad51), and genes whose products interact with the aforementioned gene products. See, e.g., Klutstein et al. *Genetics.* 2008 April; 178(4): 2389-97.

Similarly ZFP-functional domain fusions can be used, in combination with the methods and compositions disclosed herein, to repress expression of genes involved in non-homologous end joining (e.g., Ku70/80, XRCC4, poly(ADP ribose) polymerase, DNA ligase 4). See, for example, Riha et al. (2002) *EMBO* 21:2819-2826; Freisner et al. (2003) *Plant J.* 34:427-440; Chen et al. (1994) *European Journal of Biochemistry* 224:135-142. Methods for activation and repression of gene expression using fusions between a zinc finger binding domain and a functional domain are disclosed, for example, in co-owned U.S. Pat. Nos. 6,534,261; 6,824,978 and 6,933,113. Additional repression methods include the use of antisense oligonucleotides and/or small interfering RNA (siRNA or RNAi) or shRNAs targeted to the sequence of the gene to be repressed.

Further increases in efficiency of targeted recombination, in cells comprising a zinc finger/nuclease fusion molecule and a donor DNA molecule, are achieved by blocking the cells in the $G_2$ phase of the cell cycle, when homology-driven repair processes are maximally active. Such arrest can be achieved in a number of ways. For example, cells can be treated with e.g., drugs, compounds and/or small molecules which influence cell-cycle progression so as to arrest cells in $G_2$ phase. Exemplary molecules of this type include, but are not limited to, compounds which affect microtubule polymerization (e.g., vinblastine, nocodazole, Taxol), compounds that interact with DNA (e.g., cis-platinum(II) diamine dichloride, Cisplatin, doxorubicin) and/or compounds that affect DNA synthesis (e.g., thymidine, hydroxyurea, L-mimosine, etoposide, 5-fluorouracil). Additional increases in recombination efficiency are achieved by the use of histone deacetylase (HDAC) inhibitors (e.g., sodium butyrate, trichostatin A) which alter chromatin structure to make genomic DNA more accessible to the cellular recombination machinery.

Additional methods for cell-cycle arrest include overexpression of proteins which inhibit the activity of the CDK cell-cycle kinases, for example, by introducing a cDNA encoding the protein into the cell or by introducing into the cell an engineered ZFP which activates expression of the gene encoding the protein. Cell-cycle arrest is also achieved by inhibiting the activity of cyclins and CDKs, for example, using RNAi Methods (e.g., U.S. Pat. No. 6,506,559) or by introducing into the cell an engineered ZFP which represses expression of one or more genes involved in cell-cycle progression such as, for example, cyclin and/or CDK genes. See, e.g., co-owned U.S. Pat. No. 6,534,261 for methods for the synthesis of engineered zinc finger proteins for regulation of gene expression.

Alternatively, in certain cases, targeted cleavage is conducted in the absence of a donor polynucleotide (preferably in S or $G_2$ phase), and recombination occurs between homologous chromosomes.

Expression Vectors

A nucleic acid encoding one or more fusion proteins (e.g., ZFNs) as described herein can be cloned into a vector for transformation into prokaryotic or eukaryotic cells for replication and/or expression. Vectors can be prokaryotic vectors, e.g., plasmids, or shuttle vectors, insect vectors, or eukaryotic vectors. A nucleic acid encoding a fusion protein can also be cloned into an expression vector, for administration to a cell.

To express the fusion proteins (e.g., ZFNs), sequences encoding the fusion proteins are typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989; $3^{rd}$ ed., 2001); Kriegler, *Gene Transfer and Expression: A Laboratory Manual* (1990); and *Current Protocols in Molecular Biology* (Ausubel et al., supra. Bacterial expression systems for expressing the ZFP are available in, e.g., *E. coli, Bacillus* sp., and *Salmonella* (Palva et al., *Gene* 22:229-235 (1983)). Kits for such expression systems are commercially available. Eukaryotic expression systems for mammalian cells, yeast, and insect cells are well known by those of skill in the art and are also commercially available.

The promoter used to direct expression of a fusion protein-encoding nucleic acid depends on the particular application. For example, a strong constitutive promoter suited to the host cell is typically used for expression and purification of fusion proteins.

In contrast, when a fusion protein is administered in vivo for regulation of a plant gene (see, "Nucleic Acid Delivery to Plant Cells" section below), either a constitutive, regulated (e.g., during development, by tissue or cell type, or by the environment) or an inducible promoter is used, depending on the particular use of the fusion protein. Non-limiting examples of plant promoters include promoter sequences derived from *A. thaliana* ubiquitin-3 (ubi-3) (Callis, et al., 1990, *J. Biol. Chem.* 265-12486-12493); *A. tumifaciens* mannopine synthase (Δmas) (Petolino et al., U.S. Pat. No. 6,730,824); and/or Cassava Vein Mosaic Virus (CsVMV) (Verdaguer et al., 1996, *Plant Molecular Biology* 31:1129-1139). See, also, Examples.

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to a nucleic acid sequence encoding the fusion protein, and signals required, e.g., for efficient polyadenylation of the transcript, transcriptional termination, ribosome binding sites, or translation termination. Additional elements of the cassette may include, e.g., enhancers, heterologous splicing signals, and/or a nuclear localization signal (NLS).

The particular expression vector used to transport the genetic information into the cell is selected with regard to the intended use of the fusion proteins, e.g., expression in plants, animals, bacteria, fungus, protozoa, etc. (see expression vectors described below). Standard bacterial and animal expression vectors are known in the art and are described in detail, for example, U.S. Patent Publication 20050064474A1 and International Patent Publications WO05/084190, WO05/014791 and WO03/080809.

Standard transfection methods can be used to produce bacterial, mammalian, yeast or insect cell lines that express large quantities of protein, which can then be purified using standard techniques (see, e.g., Colley et al., *J. Biol. Chem.* 264:17619-17622 (1989); *Guide to Protein Purification, in Methods in Enzymology,* vol., 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds., 1983).

Any of the well known procedures for introducing foreign nucleotide sequences into such host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Nucleic Acid Delivery to Plant Cells

As noted above, DNA constructs may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al. (1987) *Nature* 327:70-73). Alternatively, the DNA construct can be introduced into the plant cell via nanoparticle transformation (see, e.g., U.S. patent application Ser. No. 12/245,685, which is incorporated herein by reference in its entirety). Alternatively, the DNA constructs may be combined with suitable T-DNA border/flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al. (1984) *Science* 233:496-498, and Fraley et al. (1983) *Proc. Nat'l. Acad. Sci. USA* 80:4803.

In addition, gene transfer may be achieved using non-Agrobacterium bacteria or viruses such as *Rhizobium* sp. NGR234, *Sinorhizoboium meliloti, Mesorhizobium loti,* potato virus X, cauliflower mosaic virus and cassava vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of a T-strand containing the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al. (1985) *Science* 227: 1229-1231). Generally, the *Agrobacterium* transformation system is used to engineer dicotyledonous plants (Bevan et al. (1982) *Ann. Rev. Genet* 16:357-384; Rogers et al. (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al. (1984) *EMBO J* 3:3039-3041; Hooykass-Van Slogteren et al. (1984) *Nature* 311:763-764; Grimsley et al. (1987) *Nature* 325:1677-179; Boulton et al. (1989) *Plant Mol. Biol.* 12:31-40; and Gould et al. (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

The disclosed methods and compositions can be used to insert exogenous sequences into the multiple insertion site that has been inserted into the genome of a plant cell. This is useful inasmuch as expression of an introduced transgene into a plant genome depends critically on its integration site. Accordingly, genes encoding, e.g., herbicide tolerance, insect resistance, nutrients, antibiotics or therapeutic molecules can be inserted, by targeted recombination, into regions of a plant genome favorable to their expression.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna,* and *Zea*.

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 and PAT proteins using an ELISA assay is described in U.S. patent application Ser. No. 11/587,893 which reference is hereby incorporated by reference in its entirety herein. The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

Fusion proteins (e.g., ZFNs) and expression vectors encoding fusion proteins can be administered directly to the plant for gene regulation, targeted cleavage, and/or recombination. In certain embodiments, the plant contains multiple paralogous target genes. Thus, one or more different fusion proteins or expression vectors encoding fusion proteins may be administered to a plant in order to target one or more of these paralogous genes (e.g. Zp15, see PCT patent publication WO2010077319) genes in the plant.

Administration of effective amounts is by any of the routes normally used for introducing fusion proteins into ultimate contact with the plant cell to be treated. The ZFPs are administered in any suitable manner, preferably with acceptable carriers. Suitable methods of administering such modulators are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of carriers that are available.

Delivery to Mammalian Cells

The ZFNs described herein may be delivered to a target mammalian cell by any suitable means, including, for example, by injection of ZFN mRNA. See, Hammerschmidt et al. (1999) *Methods Cell Biol.* 59:87-115

Methods of delivering proteins comprising zinc-fingers are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

ZFNs as described herein may also be delivered using vectors containing sequences encoding one or more of the ZFNs. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more ZFN encoding sequences. Thus, when one or more pairs of ZFNs are introduced into the cell, the ZFNs may be carried on the same vector or on different vectors. When multiple vectors are used, each vector may comprise a sequence encoding one or multiple ZFNs.

Conventional viral and non-viral based gene transfer methods can be used to introduce nucleic acids encoding engineered ZFPs into mammalian cells. Such methods can also be used to administer nucleic acids encoding ZFPs to mammalian cells in vitro. In certain embodiments, nucleic acids encoding ZFPs are administered for in vivo or ex vivo uses.

Non-viral vector delivery systems include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids. Viral vector delivery systems include DNA and RNA viruses, which have either episomal or integrated genomes after delivery to the cell. Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386, 4,946,787; and 4,897,355) and lipofection reagents are sold commercially (e.g., TRANSFECTAM™ and LIPOFECTIN™). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

As noted above, the disclosed methods and compositions can be used in any type of mammalian cell. The proteins (e.g., ZFPs), polynucleotides encoding same and compositions comprising the proteins and/or polynucleotides described herein may be delivered to a target cell by any suitable means. Suitable cells include but are not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells, neuronal stem cells and mesenchymal stem cells.

EXAMPLES

Example 1

Plasmid Designs

Example 1.1 eZFN Binding Sites

Eight engineered zinc finger nuclease (eZFN) binding sites (CL:AR—SEQ ID NO:1, RL:PR—SEQ ID NO:2, AL:PR—SEQ ID NO:3, PL:AR—SEQ ID NO:4, CL:RR—SEQ ID NO:5, RL:CR—SEQ ID NO:6, CL:PR—SEQ ID NO:7, RL:AR—SEQ ID NO:8) were combined into a single DNA fragment (multi-eZFN binding site) with flanking PCR primer sites unique to each of the eZFN binding sites. In addition, other eZFN binding sites have been designed and shown to cleave at high levels in yeast (see, e.g., U.S. Patent Publication No. 2009/0111119), including: PL:RR—SEQ ID NO:9, AL:RR—SEQ ID NO:10, AL:CR—SEQ ID NO:11, PL:CR—SEQ ID NO:12 and Homodimer eZFN's RR:RR—SEQ ID NO:13, RL:RL—SEQ ID NO:14, PR:PR—SEQ ID NO:15, PL:PL—SEQ ID NO:16, CL:CL—SEQ ID NO:17, CR:CR—SEQ ID NO:18, AR:AR—SEQ ID NO:19, and AL:AL—SEQ ID NO:20. "CL" and "CR" refer, respectively, to the "left" and "right" hand zinc finger designs for the CCR5 receptor designated 8266 and 8196, which have the sequences and bind to the target sites shown in U.S. Patent Publication No. 2008/0159996. "AL" and "AR" refer, respectively, to the "left" and "right" hand zinc finger designs for the AAVS1 locus designated 15556 and 15590 and have the recognition helix sequences and bind to the target sites shown in U.S. Patent Publication No. 2008/0299580. The recognition helix sequences and target sites for the "PL" and "PR" designs, as well as the "RL" and "RR" designs are listed below in Tables 1 and 2. PL and PR both refer to the "left" and "right" hand zinc finger designs for ZFNs specific for the human PRMT1 gene, while "RL" and "RR" refer to the "left" and "right" hand zinc finger designs for ZFNs specific for the mouse Rosa26 locus.

None of these target sites are present in the maize genome as gauged by bioinformatic analysis. The PCR primer sites were included for evaluation of NHEJ resulting from double-strand cleavage of the chromosomally-localized DNA fragment by the eZFNs.

TABLE 1

| ZFN Name (gene) | F1 | F2 | F3 | F4 | F5 | F6 |
|---|---|---|---|---|---|---|
| ZFN 19353 (PRMT) "PL" | DRSNLSR (SEQ ID NO: 46) | RSDALTQ (SEQ ID NO: 47) | TSGNLTR (SEQ ID NO: 48) | TSGSLTR (SEQ ID NO: 49) | TSGHLSR (SEQ ID NO: 50) | N/A |
| ZFN 19354 (PRMT) "PR" | RSANLSV (SEQ ID NO: 51) | DRANLSR (SEQ ID NO: 52) | RSDNLRE (SEQ ID NO: 53) | ERGTLAR (SEQ ID NO: 54) | TSSNRKT (SEQ ID NO: 55) | N/A |

ZFN Designs

TABLE 1-continued

ZFN Designs

| ZFN Name (gene) | | F1 | F2 | F3 | F4 | F5 | F6 |
|---|---|---|---|---|---|---|---|
| ZFN 18473 (mRosa26) | "RL" | DRSARTR (SEQ ID NO: 56) | QSGHLSR (SEQ ID NO: 57) | RSDDLSK (SEQ ID NO: 58) | RNDHRKN (SEQ ID NO: 59) | N/A | N/A |
| ZFN 18477 (mRosa26) | "RR" | QSGDLTR (SEQ ID NO: 60) | TSGSLTR (SEQ ID NO: 61) | QSGHLAR (SEQ ID NO: 62) | QSSDLTR (SEQ ID NO: 63) | RSDNLSE (SEQ ID NO: 64) | QNAHRKT (SEQ ID NO: 65) |

TABLE 2

ZFN target binding sites

| ZFN Name (gene) | Target Binding Site |
|---|---|
| ZFN 19353 (PRMT) "PL" | acGGTGTTGAGcATGGACtcgtagaaga (SEQ ID NO: 66) |
| ZFN 19354 (PRMT) "PR" | tcTATGCCCGGGACAAGtggctggtgag (SEQ ID NO: 67) |
| ZFN 18473 (mRosa26) "RL" | gaTGGGCGGGAGTCttctgggcaggctt (SEQ ID NO: 68) |
| ZFN 18477 (mRosa26) "RR" | ctAGAAAGACTGGAGTTGCAgatcacga (SEQ ID NO: 69) |

Att sites were included in the synthesized DNA fragment and the fragment cloned into a plasmid using TOPO cloning (Invitrogen, Carlsbad, Calif.). The Gateway LR CLONASE™ (Invitrogen) reaction was used to transfer this fragment into pDAB101834 and pDAB101849. These vectors contain selectable markers suitable for tobacco and maize, respectively. pDAB101834 is comprised of the Cassava Vein Mosaic Virus promoter (CsVMV; promoter and 5' untranslated region derived from the cassava vein mosaic virus; Verdaguer et al., (1996) *Plant Molecular Biology*, 31(6) 1129-1139), the phosphinothricin acetyl transferase gene (PAT; Wohlleben et al., (1988) *Gene* 70(1), 25-37) and the AtuORF1 3' UTR (3' untranslated region (UTR) comprising the transcriptional terminator and polyadenylation site of open reading frame 1 (ORF1) of *Agrobacterium tumefaciens* pTi15955; Barker et al., (1983) *Plant Molecular Biology*, 2(6), 335-50). The maize pDAB101849 vector contains the selectable marker cassette including the rice actin 1 gene promoter (OsAct1; promoter, 5' untranslated region (UTR) and intron derived from the *Oryza sativa* actin 1 (Act1) gene; McElroy et al., (1990) *Plant Cell* 2(2):163-71) and the ZmLip 3' UTR (3' untranslated region (UTR) comprising the transcriptional terminator and polyadenylation site of the *Zea mays* LIP gene; GenBank accession L35913).

Figure 7:
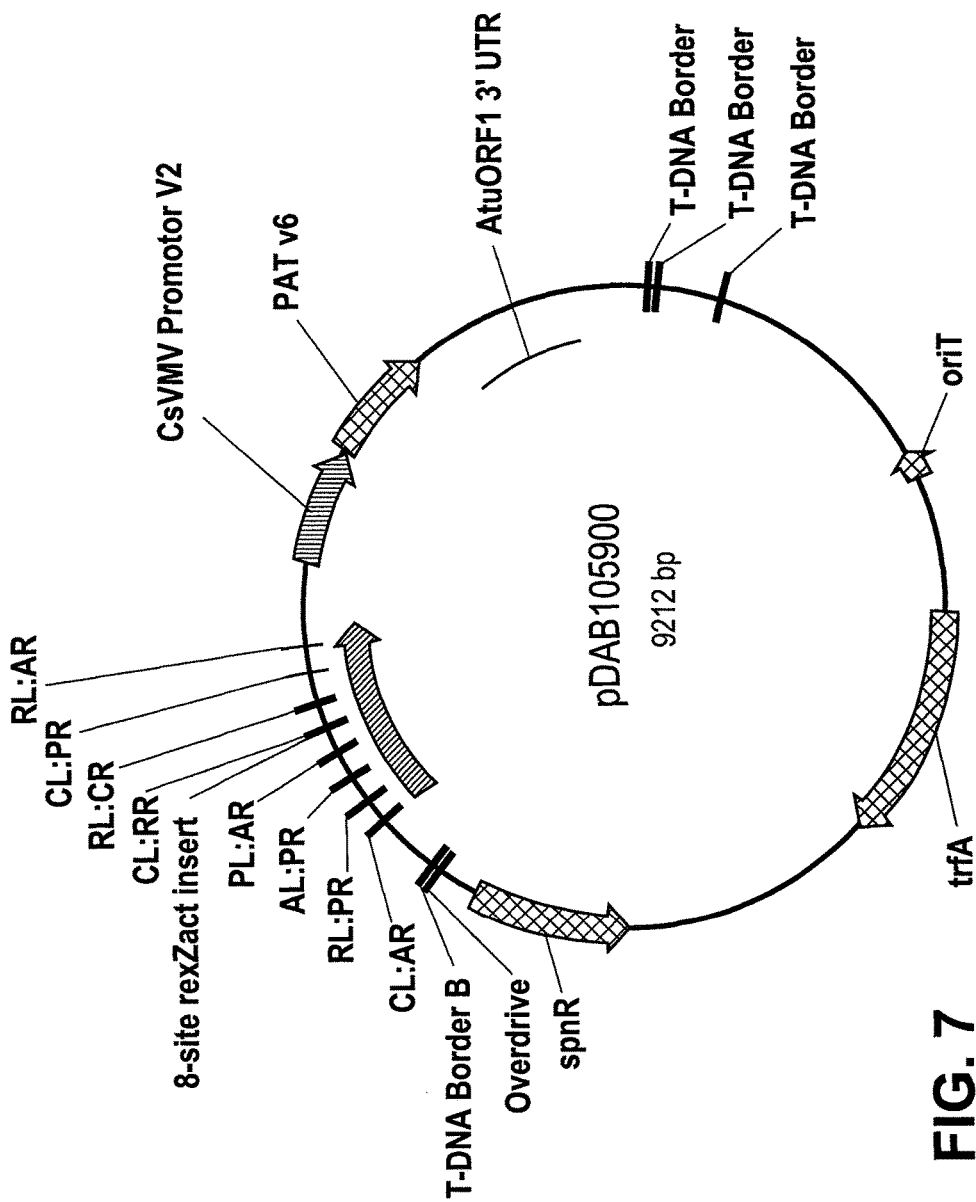
FIG. 7 is a plasmid map of pDAB105900.
Figure 8:
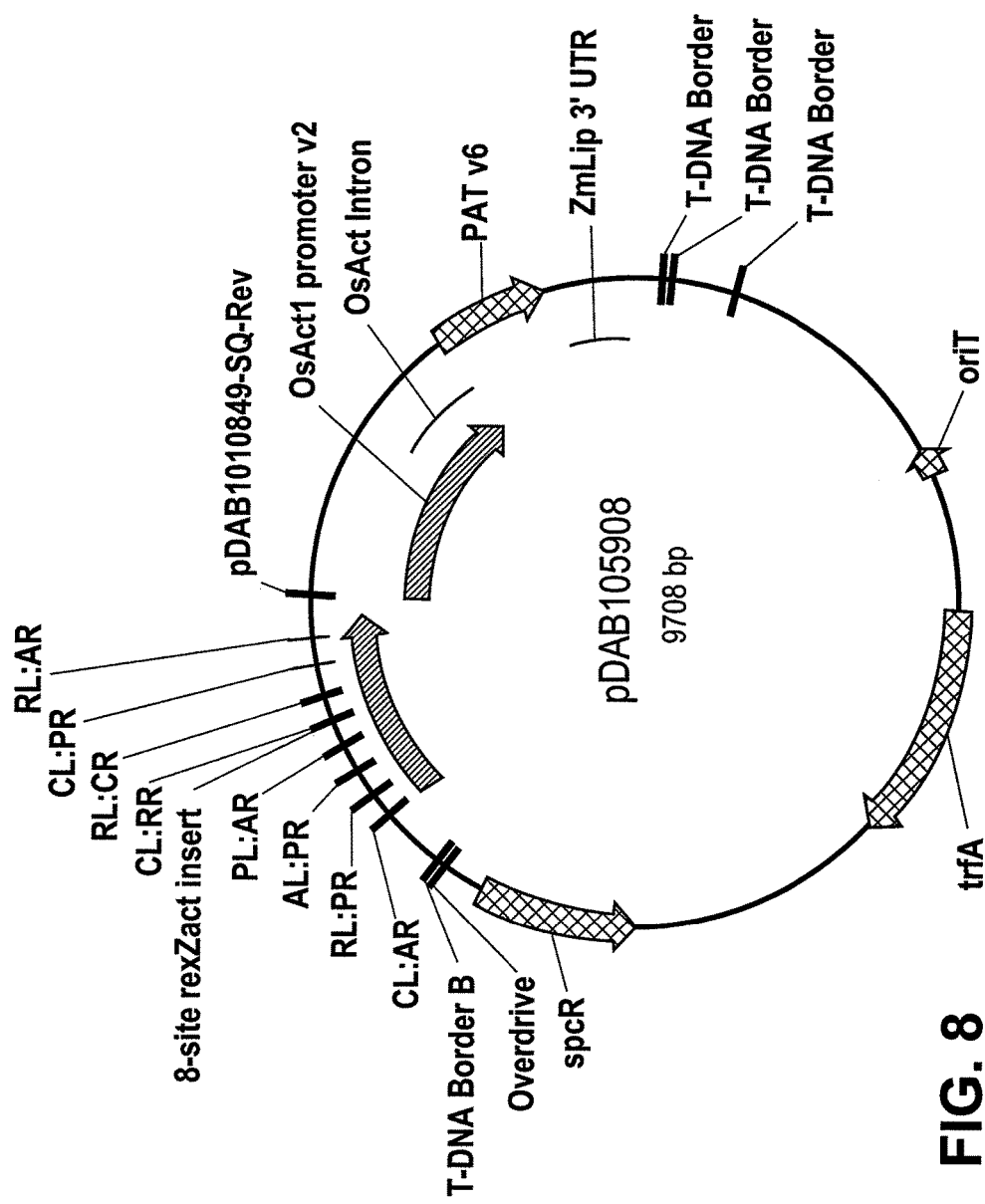
FIG. 8 is a plasmid map of pDAB105908.

The resultant tobacco vector, pDAB105900 (FIG. 7), was transferred into *Agrobacterium tumefaciens* using electroporation. After restriction enzyme validation, the *Agrobacterium* was stored as glycerol stocks until used. The maize vector, pDAB105908 (FIG. 8), was bulked and purified using the Qiagen QIAfilter Plasmid Giga kit (Qiagen, Valencia, Calif.) according to the manufacturer's protocol.

Example 1.2

Vectors for Expressing eZFNs

ZFN vectors expressing the appropriate recognition helices in either a canonical (C2H2) or non-canonical (C3H) backbone were prepared essentially as described in U.S. Patent Publication Nos. 2008/0182332 and 2008/0159996.

The function of the ZFNs was tested on the eZFN multiple insertion site as described in Example 1.1 inserted into a yeast ZFN screening system (see, U.S. Patent Publication No. 2009/0111119). All ZFN pairs tested were active in the yeast system.

Figure 9:
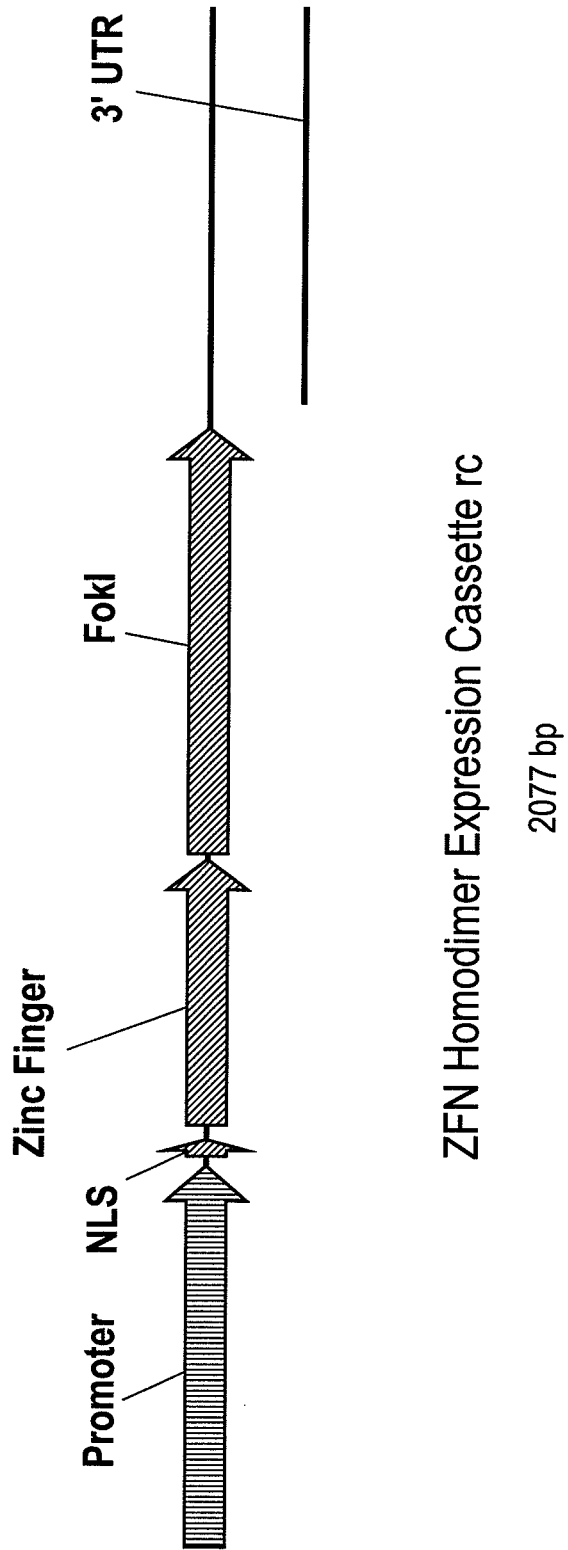
FIG. 9 is a diagram of the Zinc Finger Nuclease Homodimer expression cassette.
Figure 10:
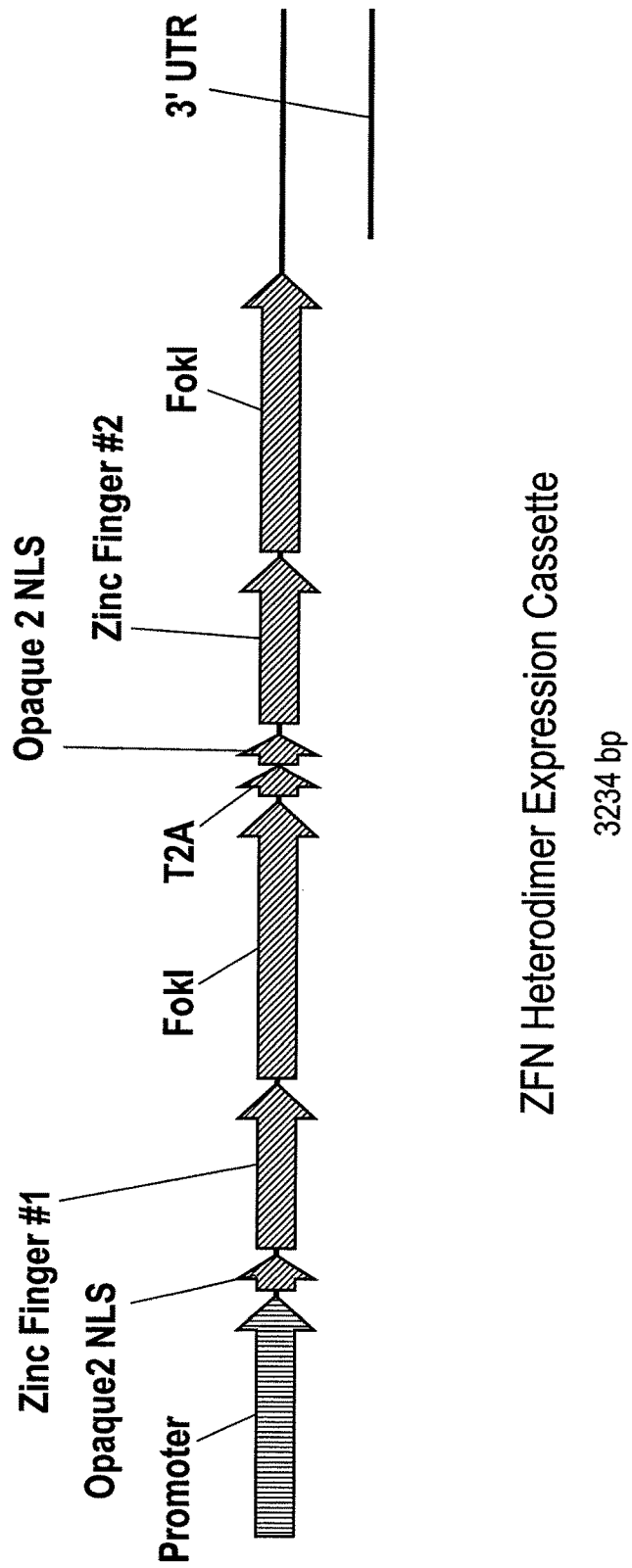
FIG. 10 is a diagram of the Zinc Finger Nuclease Heterodimer expression cassette.

Eight eZFNs are cloned into vectors which contain the regulatory sequences necessary for expression in plant cells. The cloning strategies deployed for the constructions are as essentially described in U.S. Patent Publication Nos. 2009/0111188A1 and 20100199389. FIGS. 9 and 10 show schematics of generalized eZFN expression cassettes.

Example 2

Evaluation of eZFNs in Maize

Example 2.1

WHISKERS™-Mediated DNA Delivery

Embryogenic Hi-II cell cultures of maize were produced, and were used as the source of living plant cells in which integration was demonstrated. One skilled in the art may envision the utilization of cell cultures derived from a variety of plant species, or differentiated plant tissues derived from a variety of plant species, as the source of living plant cells in which integration was demonstrated.

In this example, a plasmid (pDAB105908) containing a PAT plant selectable marker cassette and the multi-eZFN binding site insert sequence was used to generate transgenic events. The transgenic isolates were transformed with eZFNs to evaluate double strand cleavage.

In particular, 12 ml packed cell volume (PCV) from a previously cryo-preserved cell line plus 28 ml of conditioned medium was subcultured into 80 ml of GN6 liquid medium (N6 medium (Chu et al. (1975) *Scientia Sin* 18:659-668), 2.0 mg/L 2,4-D, 30 g/L sucrose, pH 5.8) in a 500 ml Erlenmeyer flask, and placed on a shaker at 125 rpm at 28° C. This step was repeated 2 times using the same cell line such that a total of 36 ml PCV was distributed across 3 flasks. After 24 hours the GN6 liquid media was removed and replaced with 72 ml GN6 S/M osmotic medium (N6 Medium, 2.0 mg/L 2,4-D, 30 g/L sucrose, 45.5 g/L sorbitol, 45.5 g/L mannitol, 100 mg/L myo-inositol, pH 6.0). The flask was incubated in the dark for 30-35 minutes at 28° C. with moderate agitation (125 rpm). During the incubation period, a 50 mg/ml suspension of silicon carbide whiskers (Advanced Composite Materials, LLC, Greer, S.C.) was prepared by adding 8.1 ml of GN6 S/M liquid medium to 405 mg of sterile, silicon carbide whiskers.

Following incubation in GN6 S/M osmotic medium, the contents of each flask were pooled into a 250 ml centrifuge bottle. After all cells in the flask settle to the bottom, content volume in excess of approximately 14 ml of GN6 S/M liquid was drawn off and collected in a sterile 1-L flask for future use. The pre-wetted suspension of whiskers was mixed at maximum speed on a vortex for 60 seconds, and then added to the centrifuge bottle.

In this example, 170 µg of purified fragment from pDAB105908 plasmid DNA was added to each bottle. Once DNA was added, the bottle was immediately placed in a modified Red Devil 5400 commercial paint mixer (Red Devil Equipment Co., Plymouth, Minn.) and agitated for 10 seconds. Following agitation, the cocktail of cells, media, whiskers and DNA was added to the contents of a 1-L flask along with 125 ml fresh GN6 liquid medium to reduce the osmoticant. The cells were allowed to recover on a shaker set at 125 rpm for 2 hours. Six mL of dispersed suspension was filtered onto Whatman #4 filter paper (5.5 cm) using a glass cell collector unit connected to a house vacuum line such that 60 filters were obtained per bottle. Filters were placed onto 60×20 mm plates of GN6 solid medium (same as GN6 liquid medium except with 2.5 g/L Gelrite gelling agent) and cultured at 28° C. under dark conditions for 1 week.

Example 2.2

Identification and Isolation of Putative Transgenic Events

One week post-DNA delivery, filter papers were transferred to 60×20 mm plates of GN6 (1H) selection medium (N6 Medium, 2.0 mg/L 2,4-D, 30 g/L sucrose, 100 mg/L myo-inositol, 2.5 g/L Gelrite, pH 5.8) containing a selective agent. These selection plates were incubated at 28° C. for one week in the dark. Following one week of selection in the dark, the tissue was embedded onto fresh media by scraping half the cells from each plate into a tube containing 3.0 mL of GN6 agarose medium held at 37-38° C. (N6 medium, 2.0 mg/L 2,4-D, 30 g/L sucrose, 100 mg/L myo-inositol, 7 g/L SeaPlaque agarose, pH 5.8, autoclaved for only 10 minutes at 121° C.).

The agarose/tissue mixture was broken up with a spatula, and subsequently 3 mL of agarose/tissue mixture was evenly poured onto the surface of a 100×15 mm petri dish containing GN6 (1H) medium. This process was repeated for both halves of each plate. Once all the tissue was embedded, plates were individually sealed with NESCOFILM® or PARAFILM M®, and cultured at 28° C. under dark conditions for up to 10 weeks.

Putatively transformed isolates that grow under these selection conditions were removed from the embedded plates and transferred to fresh selection medium in 60 ×20 mm plates. If sustained growth was evident after approximately 2 weeks, an event was deemed to be resistant to the applied herbicide (selective agent) and an aliquot of cells was subsequently harvested for genotype analysis.

Example 2.3

Genomic DNA Extraction

Genomic DNA (gDNA) was extracted from isolated maize cells as described in Example 2.2 and utilized as template for PCR genotyping experiments. gDNA was extracted from approximately 100-300 µl packed cell volume (PCV) of Hi-II callus that were isolated as described above according to the manufacturer's protocols detailed in the DNeasy 96 Plant Kit (QIAGEN Inc., Valencia, Calif.). Genomic DNA was eluted in 100 µl of kit-supplied elution buffer yielding final concentrations of 20-200 ng/µl and subsequently analyzed via PCR-based genotyping methods outlined below.

Example 2.4

Molecular Analysis of Copy Number

TAQMAN® assays were performed to screen samples of herbicide resistant callus to identify those that contained single copy integration of the pDAB105908 transgene. Detailed analysis was conducted using primers and probes specific to gene expression cassettes. Single copy events were identified for additional analysis.

Custom TAQMAN® assays were developed for PAT gene analysis in Hi-II callus by Third Wave Technologies (Madison, Wis.). The genomic DNA samples were first denatured in 96-well plate format by incubation at 95° C. and then cooled to ambient temperature. Next, master mix (containing probe mix for PAT and an internal reference gene, in addition to buffer) was added to each well and the samples were overlaid with mineral oil. Plates were sealed and incubated in a BioRad TETRAD® thermocycler. Plates were cooled to ambient temperature before being read on a fluorescence plate reader. All plates contained 1 copy, 2 copy and 4 copy standards as well as wild-type control samples and blank wells containing no sample. Readings were collected and compared to the fold over zero (i.e. background) for each channel was determined for each sample by the sample raw signal divided by no template raw signal.

From this data a standard curve was constructed and the best fit determined by linear regression analysis. Using the parameters identified from this fit, the apparent PAT copy number was then estimated for each sample.

Example 2.5

Primer Design for PCR Genotyping

In this example, PCR genotyping was understood to include, but not be limited to, polymerase-chain reaction (PCR) amplification of genomic DNA derived from isolated maize callus tissue predicted to contain donor DNA embedded in the genome, followed by standard cloning and sequence analysis of PCR amplification products. Methods of PCR genotyping have been well described (for example, Rios, G. et al. (2002) *Plant J.* 32:243-253) and may be applied to genomic DNA derived from any plant species or tissue type, including cell cultures.

One skilled in the art may devise strategies for PCR-genotyping that include (but are not limited to) amplification of specific sequences in the plant genome, amplification of multiple specific sequences in the plant genome, amplification of non-specific sequences in the plant genome, or combinations thereof. Amplification may be followed by cloning and sequencing, as described in this example, or by direct sequence analysis of amplification products. One skilled in the art might envision alternative methods for analysis of the amplification products generated herein. In one embodiment described herein, oligonucleotide primers specific for the gene target are employed in PCR amplifications.

In the examples presented here, an oligonucleotide primer is synthesized, e.g., by Integrated DNA Technologies, Inc. (Coralville, Iowa), under conditions of standard desalting and diluted with water to a concentration of 100 µM. The oligonucleotide primer was designed to anneal to the flanking regions of the DNA insert. The primers were tested using dilutions of the plasmid DNA in the presence of DNA isolated from non-transgenic plants. The pDAB105908 transgene was PCR amplified from genomic DNA of the putative events using the primers. The resulting fragment was cloned into a plasmid vector and sequenced to confirm that the multi-eZFN binding site sequence was completely integrated into the plant genome during the transformation.

Example 2.6

Selection of Transgenic Events with the Target DNA

Low copy (1-2) events were screened by PCR for intact multi-eZFN binding site sequence and for the PAT gene. Copy number was confirmed by Southern analysis using standard methods with a PAT gene probe. Callus from selected transgenic events harboring single copy, intact inserts were maintained for subsequent evaluation with transiently expressed eZFNs.

Example 3 eZFN DNA Delivery into Plant Cells

In order to enable eZFN-mediated double-strand cleavage, it is understood that delivery of eZFN-encoding DNA followed by expression of functional eZFN protein in the plant cell is required. One skilled in the art may envision that expression of functional ZFN protein may be achieved by several methods, including, but not limited to transgenesis of the ZFN-encoding construction, or transient expression of the ZFN-encoding construction.

In the examples cited herein, methods are described for the delivery of eZFN-encoding DNA into plant cells. One skilled in the art can use any of a variety of DNA-delivery methods appropriate for plant cells, including, but not limited to, *Agrobacterium*-mediated transformation, biolistics-based DNA delivery or WHISKERS™-mediated DNA delivery. In one embodiment described herein, biolistics-mediated DNA delivery experiments were carried out using various eZFN-encoding DNA constructions.

Example 3.1

Biolistic-Mediated DNA Delivery

As described above, embryogenic Hi-II cell cultures of maize were produced, and were used as the source of living plant for evaluating eZFN function. One skilled in the art may envision the utilization of cell cultures derived from a variety of plant species, or differentiated plant tissues derived from a variety of plant species, as the source of living plant cells in which targeted integration is demonstrated.

Plasmids expressing one of eight eZFNs that bind at a specific target sequence on the multi-eZFN binding site, together with an internal control (IPK-1), were bombarded into a pool of callus from 5-10 transgenic isolates.

The transgenic Hi-II maize callus events were subcultured weekly on GN6 (1H) medium. Seven days post culture, approximately 400 mg of cells were thinly spread in a circle 2.5 cm in diameter over the center of a 100×15 mm petri dish containing GN6 S/M media solidified with 2.5 g/L gelrite. The cells were cultured under dark conditions for 4 hours. To coat the biolistic particles with DNA, 3 mg of 0.6 micron diameter gold particles were washed once with 100% ethanol, twice with sterile distilled water and resuspended in 50 µl water in a siliconized Eppendorf tube. A total of 5 µg of plasmid DNA, 20 µl spermidine (0.1 M) and 50 µl calcium chloride (2.5 M) were added separately to the gold suspension and gently mixed on a vortex. The mixture was incubated at room temperature for 10 min, pelleted at 10,000 rpm in a benchtop microcentrifuge for 10 seconds, resuspended in 60 µl cold 100% ethanol, and 8-9 µl was distributed onto each macrocarrier.

Bombardment was performed using the Biolistic PDS-1000/HE™ system (Bio-Rad Laboratories, Hercules, Calif.). Plates containing the cells were placed on the middle shelf under conditions of 1100 psi and 27 inches of Hg vacuum, and were bombarded following the operational manual. Twenty four hours post-bombardment, the tissue was transferred in small clumps to GN6 solid medium.

Example 4

Solexa Sequencing and Analysis

Example 4.1

Sample Preparation

Seventy two hours after bombardment with the eZFNs and a control IPK1-ZFN (Shukla et al. (1990) *Nature* 459, 437-441), tissue was collected in 2 mL microfuge tubes and lyophilized for at least 48 hrs. Genomic DNA was extracted from lyophilized tissue using a QIAGEN®gDNA extraction kit according to manufacturer's specifications. Finally, DNA was resuspended in 200 µl of water and concentration was determined using a Nanodrop spectrophotometer (Thermo Scientific, Wilmington, Del.). Integrity of the DNA was estimated by running all samples on 0.8% agarose E-gels (Invitrogen, Carlsbad, Calif.). All samples were normalized (25 ng/ul) for PCR amplification to generate amplicons for Solexa sequencing.

PCR primers for amplification of regions encompassing each of the eZFN cleavage sites as well as the IPK1-ZFN target site from targeted (ZFN-treated) and control samples were purchased from IDT (Integrated DNA Technologies, San Jose, Calif.). Optimum amplification conditions for these primers were identified by gradient PCR using 0.2 µM appropriate primers, the Accuprime Pfx Supermix (1.1×, Invitrogen, Carlsbad, Calif.) and 100 ng of template genomic DNA in a 23.5 µL reaction. Cycling parameters include an initial denaturation at 95° (5 min) followed by 35 cycles of denaturation (95° C., 15 sec), annealing [55-72° C., 30 sec], extension (68° C., 1 min) and a final extension (72° C., 7 min). Amplification products were analyzed on 3.5% TAE agarose gels. After identifying an optimum annealing temperature, preparative PCR reactions were carried out to validate each set of PCR primers and for generating the Solexa amplicon. Oligonucleotides used for amplification of eZFN targeting regions in maize and tobacco are shown in Table 3 below. IPK1 targeting regions were amplified using the primers (SEQ ID NO: 27 GCA-GTGCATGTTATGAGC (forward primer) and SEQ ID NO: 28 CAGGACATAAATGAACTGAATC (reverse primer)).

TABLE 3

Primer Sequences Used to Amplify the eZFN Cleavage Sites.

| Primer Name | Seq ID NO: | Sequence | Primer Name | Seq ID NO: | Sequence |
|---|---|---|---|---|---|
| SP/AL:PR | SEQ ID NO: 29 | GGCACAGAGTAAGAGGAAAA | ASP/AL:PR | SEQ ID NO: 38 | GCAGTGCTCTGTGGGGTC |
| SP/CL:AR | SEQ ID NO: 30 | AGGGACCCAGGTATACATTT | ASP/CL:AR | SEQ ID NO: 39 | CCTGGACAGTTGTCAAAATT |
| SP/CL:PR | SEQ ID NO: 31 | CATTCCGCCCTTGCCAGC | ASP/CL:PR | SEQ ID NO: 40 | GTGAACTTATTATCCATCTGTCC |
| SP/CL:RR | SEQ ID NO: 33 | GACAATGCCTGACTCCCG | ASP/CL:RR | SEQ ID NO: 41 | CACTCAGACACCAGGGTTT |
| SP/PL:AR | SEQ ID NO: 34 | CAAGGAATGAATGAAACCG | ASP/PL:AR | SEQ ID NO: 42 | AGCCGGGAGATGAGGAAG |
| SP/RL:AR | SEQ ID NO: 35 | CTGCAGGAGACAGGTGCC | ASP/RL:AR | SEQ ID NO: 43 | CCTGGGCTGCTTCACAAC |
| SP/RL:CR | SEQ ID NO: 36 | CAATCCCCACCCAACACT | ASP/RL:CR | SEQ ID NO: 44 | AGGAGGGTGATGGTGAGG |
| SP/RL:PR | SEQ ID NO: 37 | CCTGGGGAGTAGCAGTGTT | ASP/RL:PR | SEQ ID NO: 45 | TGTGATTACTACCCTGCCC |

For preparative PCR, 8-individual small scale PCR reactions were completed for each template using conditions described above and the products were pooled together and gel purified on 3.5% agarose gels using Qiagen MinElute™ gel purification kit. Concentrations of the gel purified amplicons were determined using a Nanodrop spectrophotometer, and Solexa samples were prepared by pooling approximately 100 ng of amplicons from eZFN targeted and corresponding wild type controls as well as the normalizing IPK-1 targeted and wild type controls. From the eZFN+ IPK-1 targeted samples, IPK-1 targeted sample and wild type controls, four final Solexa samples comprising amplicons were generated and sequenced. The amplicons were cloned into PCR-Blunt H-TOPO (Invitrogen) and submitted for sequencing to validate the primers prior to Solexa sequencing.

Example 4.2

Solexa Sequencing and Analysis

Solexa sequencing resulted in the production of thousands of sequences. Sequences were analyzed using DAS Next Generation Sequence (NGS) analysis scripts. Low quality sequences (sequences with a quality score cut off <5) were filtered out. The sequences were then aligned with the reference sequence and scored for insertions/deletions (Indels) at the ZFN cleavage site caused by the ZFN-mediated cleavage and NHEJ mediated repair, which often causes indels that are indicative of ZFN activity. Editing activity was determined by the number of deletions greater than one by within the "gap" sequence between the binding sites for the ZFN proteins after subtracting the background activity. The activity for each eZFN in the study was calculated compared to the wild type control and normalized to the IPK-1 ZFN activity. Normalized activities for each eZFN were then compared to rank the eZFNs used in the study. Activity was also assessed at the sequence alignment level (reference as compared to Solexa output) by the presence of indels at the eZFN cleavage site.

Figure 11:
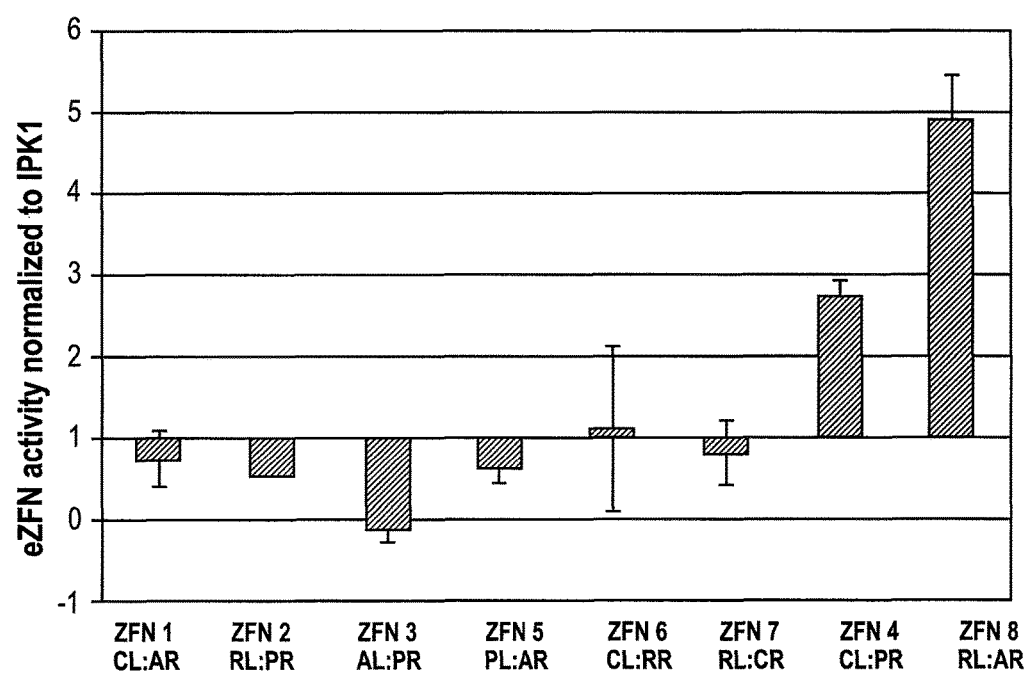
FIG. 11 shows eZFN cleavage activity in maize as determined by the frequency of deletions resulting from non-homologous end joining after cleavage.

As shown in FIG. 11, seven out of eight eZFNs show editing activity in maize.

Example 5

Evaluation of eZFNs in Tobacco

Example 5.1

Stable Integration of Multi-eZFN Binding Site Sequence

To make transgenic plant events with an integrated copy of the multi-eZFN binding site sequence described hereinabove, leaf discs (1 cm²) cut from Petit Havana tobacco plants (e.g., event 1585-10 containing a previously integrated ZFN-IL1 binding site), aseptically grown on MS medium (Phytotechnology Labs, Shawnee Mission, Kans.) and 30 g/L sucrose in PhytaTrays (Sigma, St. Louis, Mo.), were floated on an overnight culture of Agrobacterium LBA4404 harboring plasmid pDAB105900 grown to $OD_{600}$~1.2, blotted dry on sterile filter paper and then placed onto the same medium with the addition of 1 mg/L indoleacetic acid and 1 mg/L benzyamino purine in 60×20 mm dishes (5 discs per dish). Following 72 hours of co-cultivation, leaf discs were transferred to the same medium with 250 mg/L cephotaxime and 5 mg/L BASTA®. After 3-4 weeks, plantlets were transferred to MS medium with 250 mg/L cephotaxime and 10 mg/L BASTA® in PhytaTrays for an additional 2-3 weeks prior to leaf harvest and molecular analysis.

Example 5.2

Copy Number and PTU Analysis of Multi-eZFN Binding Site Sequence Transgenic Events DNA Isolation. Transgenic tobacco plant tissue was harvested from BASTA®-resistant plantlets and lyophilized for at least 2 days in 96-well collection plates. DNA was then isolated using the DNEASY™ 96 well extraction kit (Qiagen, Valencia, Calif.) following the manufacturer's instructions. A Model 2-96A Kleco tissue pulverizer (Garcia Manufacturing, Visalia Calif.) was used for tissue disruption.

DNA Quantification. Resulting genomic DNA was quantified using a QUANT-IT® Pico Green DNA assay kit (Molecular Probes, Invitrogen, Carlsbad, Calif.). Five pre-quantified DNA standards ranging from 20 ng/µL to 1.25 ng/µL (serially diluted) were used for standard curve generation. Unknown samples were first diluted 1:10 or 1:20 dilutions to be within the linear range of the assay. 5 µL of diluted samples and standards were mixed with 100 µL of diluted Pico Green substrate (1:200) and incubated for ten minutes in the dark. Fluorescence was then recorded using a Synergy2 plate reader (Biotek, Winooski, Vt.). Genomic DNA concentration were estimated from the standard curve calculated after background fluorescence corrections. Using TE or water, DNA was then diluted to a common concentration of 10 ng/µL using a Biorobot3000 automated liquid handler (Qiagen).

Copy Number Estimation. Putative transgenic events were analyzed for integration complexity using multiplexed DNA hydrolysis probe assays which is analogous to TAQMAN® assays. Copy number of the multi-site construct was estimated using sequence specific primers and probes for both the PAT transgene and an endogenous tobacco reference gene, PAL. Assays for both genes were designed using LIGHTCYCLER® Probe Design Software 2.0 Real time PCR for both genes was evaluated using the LIGHTCYCLER®480 system (Roche Applied Science, Indianapolis, Ind.). For amplification, LIGHTCYCLER®480 Probes Master mix was prepared at 1× final concentration in a 10 µL volume multiplex reaction containing 0.4 µM of each primer and 0.2 µM of each probe (Table 4 below). A two step amplification reaction is performed with an extension at 58° C. for 38 seconds with fluorescence acquisition. All samples were run in triplicate and the averaged Ct values were used for analysis of each sample. Analysis of real time PCR data was performed using LIGHTCYCLER® software using the relative quant module and was based on the ΔΔCt method. For this, a sample of gDNA from a single copy calibrator was included to normalize results. The single copy calibrator event was identified by Southern analysis and was confirmed to have a single insert of the PAT gene.

TABLE 4

Primers and probes used in PAT and PAL hydrolysis probe assays

| NAME | Sequence (5'-3') | Type | Probe |
|---|---|---|---|
| TQPATS (SEQ ID NO: 70) | ACAAGAGTGGATTGATGATC TAGAGAGGT (SEQ ID NO: 21) | Primer | NA |
| TQPATA (SEQ ID NO: 71) | CTTTGATGCCTATGTGACAC GTAAACAGT (SEQ ID NO: 22) | Primer | NA |
| TQPATFQ (SEQ ID NO: 72) | CY5-GGTGTTGTGGCTGGTA TTGCTTACGCTGG-BHQ2 (SEQ ID NO: 23) | Probe | Cy5 |
| TQPALS (SEQ ID NO: 73) | TACTATGACTTGATGTTGTG TGGTGACTGA (SEQ ID NO: 24) | Primer | NA |
| TQPALA (SEQ ID NO: 74) | GAGCGGTCTAAATTCCGACC CTTATTTC (SEQ ID NO: 25) | Primer | NA |

TABLE 4-continued

Primers and probes used in PAT and PAL hydrolysis probe assays

| NAME | Sequence (5'-3') | Type | Probe |
|---|---|---|---|
| TQPALFQ (SEQ ID NO: 75) | 6FAM-AAACGATGGCAGGAG TGCCCTTTTTCTATCAAT-BHQ1 (SEQ ID NO: 26) | Probe | 6FAM |

PCR. Low copy (1-2) events were subsequently screened by PCR for intact plant transcriptional unit (PTU) for the PAT gene and an intact multi-eZFN binding site.

Example 6

Testing eZFN Cleavage at the Multi-eZFN Binding Site Sequence

For testing the ability of eZFNs to facilitate targeted cleavage at the integrated multi-eZFN binding site sequence, a transient assay was used based on transient expression of eZFN-constructs via *Agrobacterium* co-cultivation of transgenic tobacco leaf discs. Leaf discs (1 cm$^2$) cut from transgenic events containing a single, full-length copy of the multi-eZFN binding site sequence-containing construct (as well as a single, full-length copy of an ZFN-IL1 construct), were floated on an overnight culture of *Agrobacterium* grown to OD$_{600}$~1.2, blotted dry on sterile filter paper and then placed onto the same medium with the addition of 1 mg/L indoleacetic acid and 1 mg/L benzyamino purine. For each eZFN tested, three treatments were used: pDAB1601 (negative control—PAT only), pDAB4346 only (positive control—ZFN-IL1 only) and pDAB4346+pDABeZFN-X (ZFN-IL1+eZFN to be tested) with twenty leaf discs per treatment.

Example 6.1

Sequence Analysis

Genomic DNA was isolated from *Agrobacterium*-treated, transgenic tobacco leaf discs using a Qiagen DNA extraction kit. All treatments were in duplicate and genomic DNA from all samples was re-suspended in 100 µL of water and concentrations were determined by the Nanodrop. Equal amounts of genomic DNA from each replicate for individual treatments was pooled together and was used as a starting template for Solexa amplicon generation.

PCR primers for amplification of regions encompassing the multi-eZFN binding site sequence and cleavage site from targeted (eZFN-treated) and control samples were from Integrated DNA Technologies (Coralville, Iowa) and were HPLC purified. Optimum amplification conditions were identified by gradient PCR using 0.2 µM appropriate primers, Accuprime Pfx Supermix (1.1×, Invitrogen, Carlsbad, Calif.) and 100 ng of template genomic DNA in a 23.5 µL reaction. Cycling parameters were initial denaturation at 95° (5 min) followed by 35 cycles of denaturation (95° C., 15 sec), annealing [55-72° C., 30 sec], extension (68° C., 1 min) and a final extension (72° C., 7 min). Amplification products were analyzed on 3.5% TAE agarose gels. After identifying an optimum annealing temperature (56.1° C.), preparative PCR reactions were carried out to validate each set of PCR primers and for generating the Solexa amplicon.

For preparative PCR, 8-individual small scale PCR reactions were done for each template using conditions described above and the products were pooled together and gel purified on 3.5% agarose gels using Qiagen MinElute gel purification-kit. Concentrations of the gel purified amplicons were determined by using a Nanodrop spectrophotometer and approximately 200 ng of each amplicon was pooled together to prepare the final Solexa sequencing sample (800 ng total sample). The amplicons were also cloned into PCR-Blunt II-TOPO and submitted for normal sequencing to validate the primers prior to Solexa sequencing. Solexa analysis (Shendure et al. (2008) *Nat. Biotechnology*, 26: 1135-1145) was performed and sequences were analyzed.

Example 6.2

Solexa Sequencing and Analysis

Figure 12:
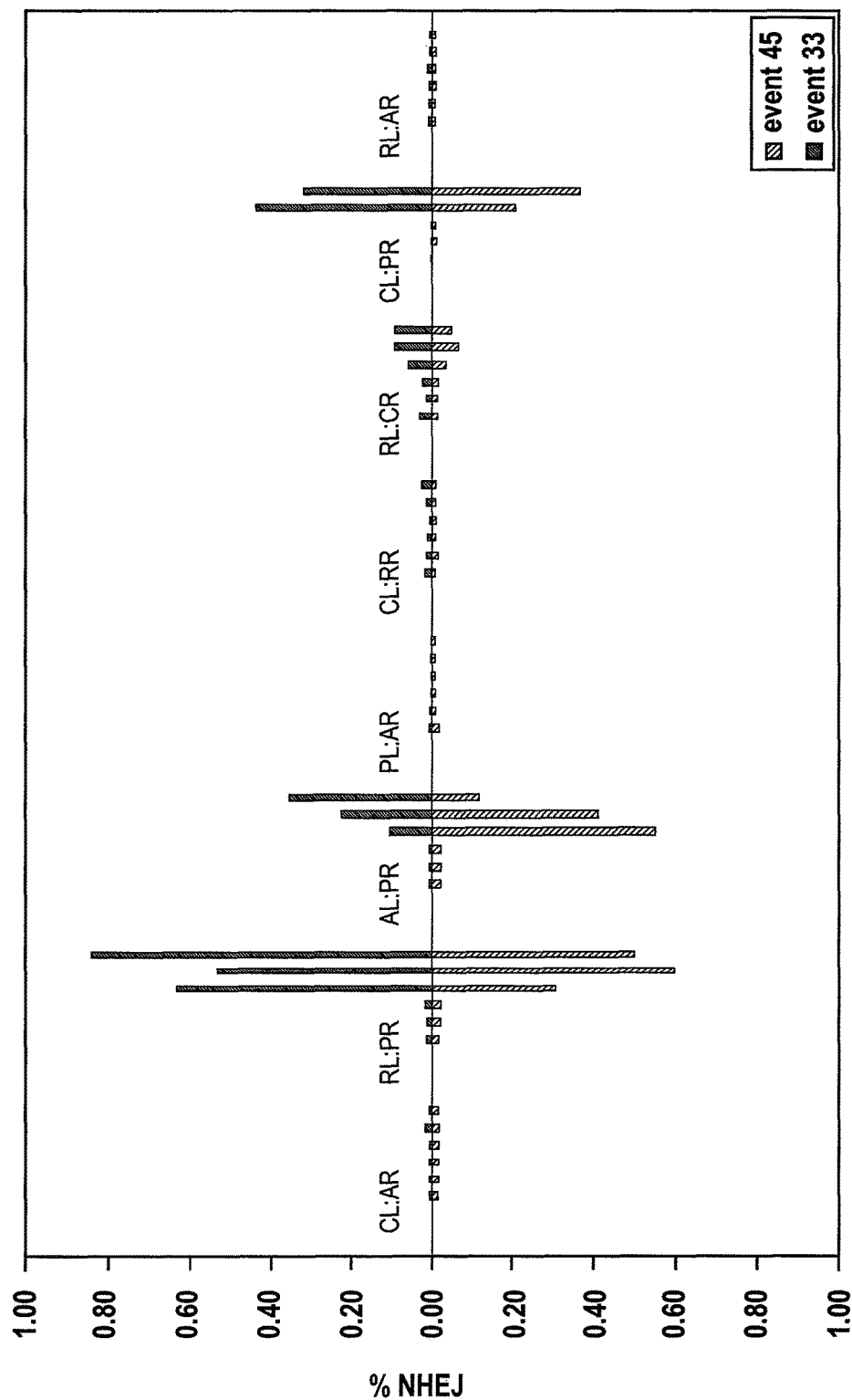
FIG. 12 shows eZFN cleavage activity in tobacco as determined by the frequency of deletions resulting from non-homologous end joining after cleavage.

Solexa sequencing was performed resulting in the production of thousands of sequences. Sequences were analyzed using DAS NGS analysis scripts. Low quality sequences (sequences with a quality score cut off <5) were filtered out. The sequences were then aligned with the reference sequence (pDAB105900 containing the multi-eZFN binding site) and scored for insertions/deletions (Indels) at the cleavage site. Editing activity (% NHEJ) for each eZFN and untreated controls was calculated (number of high quality sequences with indels/total number of high quality sequences×100) and are shown in the FIG. 12 below. Activity of the 8-eZFNs in two transgenic tobacco events, (105900/#33 and 105900/#45) was demonstrated (FIG. 12). Three of the eight eZFNs were active in the two transgenic tobacco events tested. Activity was also assessed at the sequence alignment level (reference vs solexa output) by the presence of indels at the eZFN cleavage site in eZFN treated samples.

All combinations of ZFN monomers ("right" and "left") halves were active in the yeast assay. The data described for the maize and tobacco experiments demonstrate that the some or most of the combinations are active in plants, supporting the possibility of using a significant number of the permutations of the two ZFN monomers from the four original ZFNs selected for the study.

Example 7

Intra-Allelic Recombination

Intra-allelic recombination allows the development and optimization of two independent blocks of transgenes, which can then be stacked together at one locus by recombination. To enhance the level of recombination between the two blocks, double-strand cleavage initiates DNA exchange by gene conversion or chromatid exchange.

Figure 13:
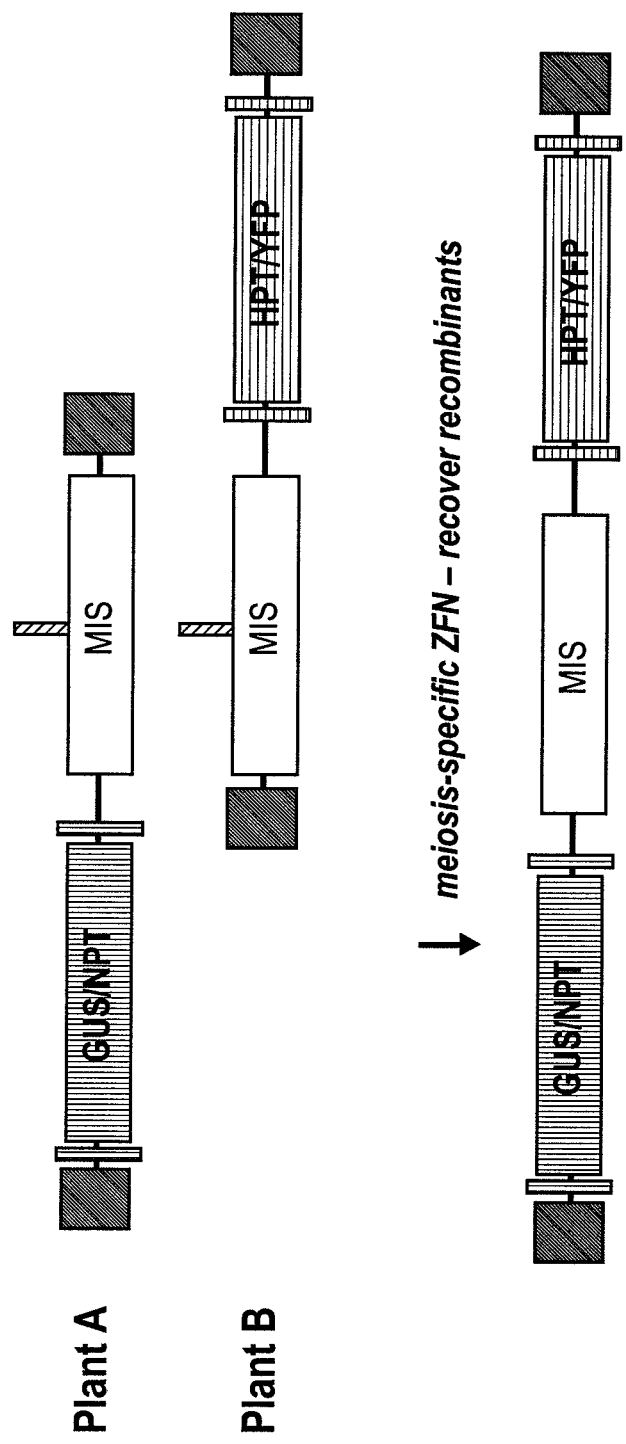
FIG. 13 is a schematic of two transgenic inserts into the same genetic locus. The top line shows random sequence labeled MIS for multiple insertion site (also referred to herein as a landing pad) containing eZFN binding sites required for the homologous recombination at the locus and Block1 comprising a kanamycin selectable marker gene and a GUS screenable marker gene. The middle line depicts the same multiple insertion site (MIS) as in the top DNA together with Block2 comprising a hygromycin resistance selectable marker gene and a yellow fluorescence protein screenable marker gene. (HPT/YFP). The bottom line depicts the locus following the recombination.

To demonstrate this concept in plants, transgenic inserts illustrated in FIG. 13 are made in *Arabidopsis thaliana*. The constructs include gene blocks which contain a selectable marker (neomycin phosphotransferase (NPTII) or hygromycin phosphotransferase (HPT) and a scorable marker (β-glucuronidase (GUS) or yellow fluorescent protein (YFP)). These gene blocks are at the identical genomic location, but displaced approximately 2 kb from each other. Recombination between the two blocks is accomplished by combining chromosomes carrying each of the two blocks into a single plant by crossing and then re-crossing the progeny to plants expressing a ZFN that cleave at a location central between the two blocks (black bar above MIS in FIG. 13). The ZFN are expressed using a meiosis specific/preferred promoter. Landing pad sequences that are used include those described in U.S. Patent Application No. 61/297,641, herein incorporated by reference.

Figure 14:
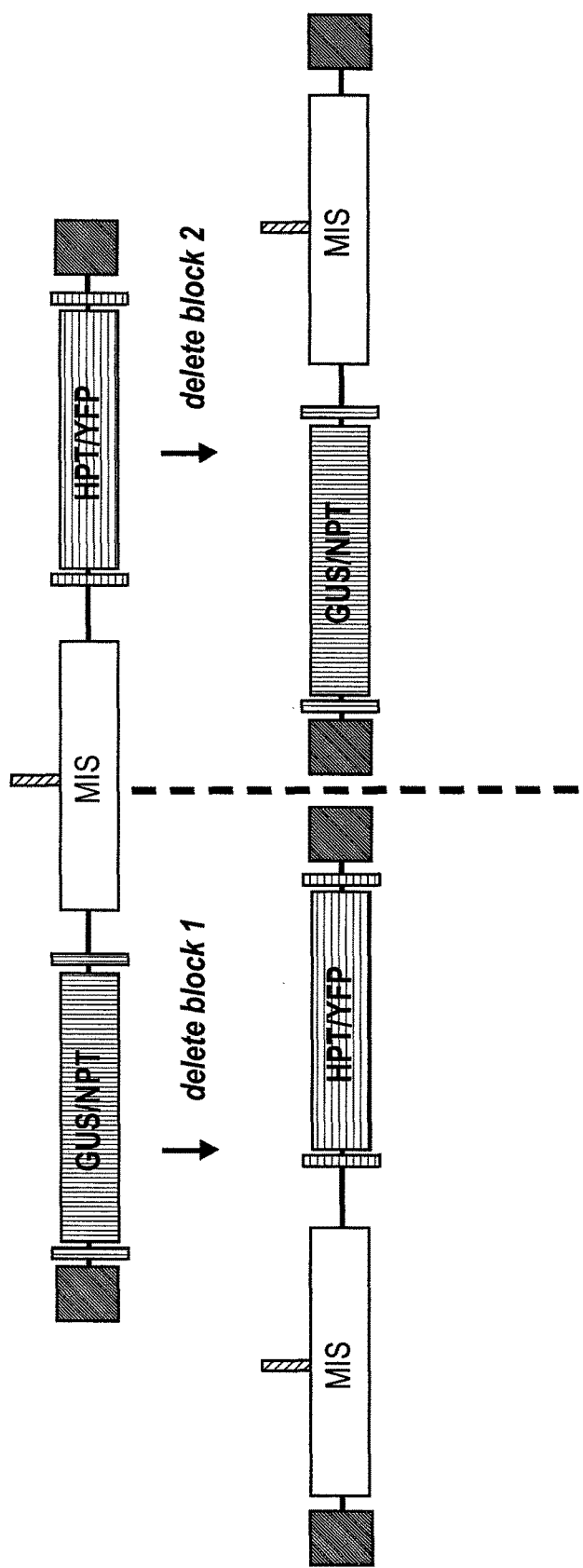
FIG. 14 shows homologous recombination at an allelic position by ZFNs and the generation of the two different DNA inserts at the same genetic locus described in FIG. 13. A construct including Block1 (comprising the kanamycin and GUC markers, GUS/NPT), a multiple insertion site (MIS or landing pad) and Block2 (comprising the hygomycin and yellow fluorescence markers, HPT/YFP) is transformed into Arabidopsis. To generate each block alone together with the multiple insertion site in separate plants, Block2 is excised from the integrated site to generate a Block1 only configuration or Block1 is excised from the integrated site to generate a Block2 only configuration. The removal of gene blocks is accomplished by crossing plants containing the original transgenic event with plants expressing ZFNs which cleave at eZFN binding sites that flank each of the gene blocks. The recovered single block plants are crossed to bring the two configurations together in a single plant and that plant is crossed to a plant expressing a meiosis-specific promoter to affect the exchange of DNA between the two Block1 and Block2 alleles.
Figure 15:
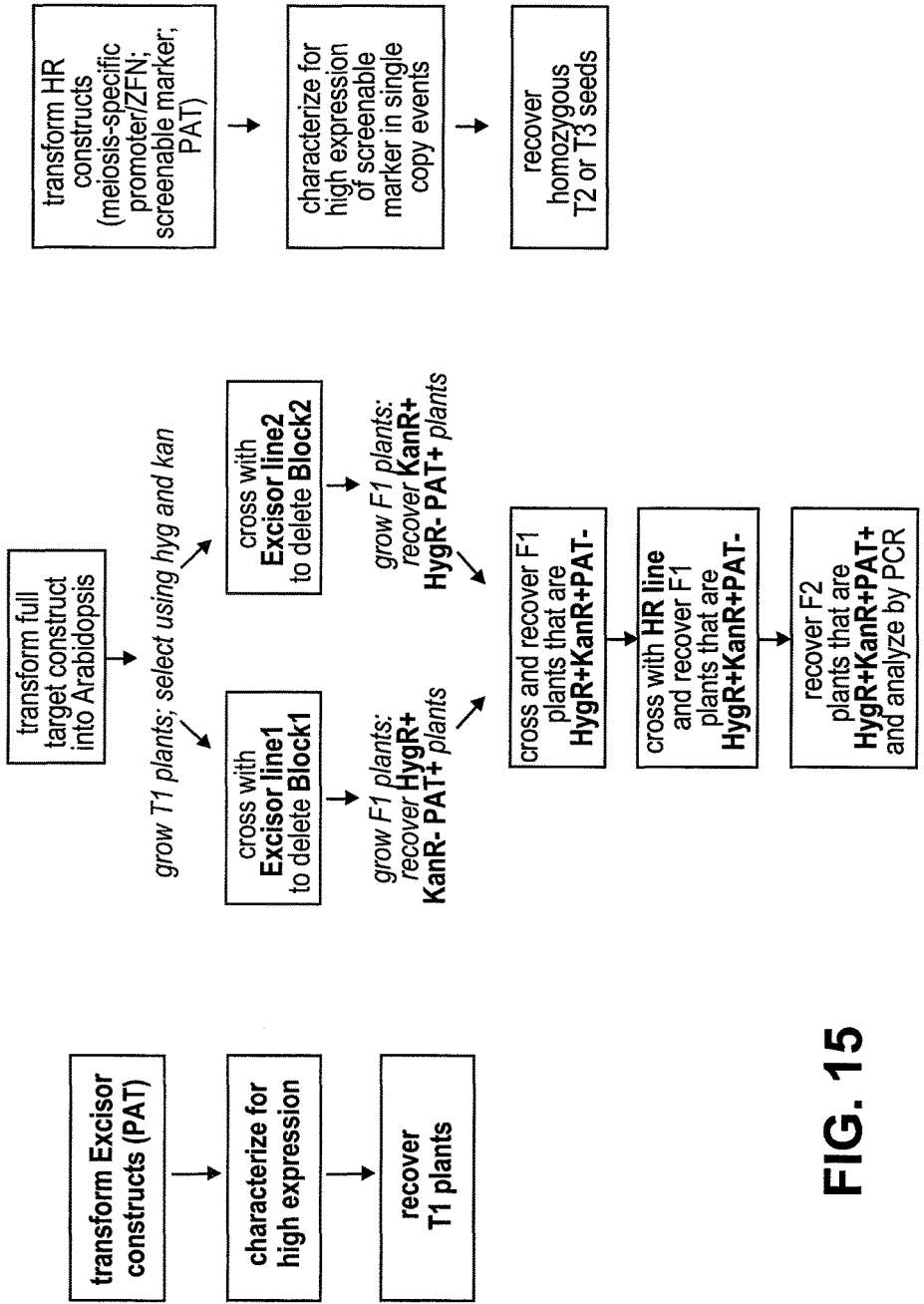
FIG. 15 is a schematic flowchart depicting the steps to obtain recombination between two DNA sequences located at the same genetic locus by ZFN cleavage at an intermediate site between the two sequences. The construct described in FIG. 16 is transformed into Arabidopsis. One of the two gene blocks (described in FIG. 14) is removed by crossing with plants expressing eZFNs whose binding sites flank the blocks, resulting in plants containing either Block1 or Block2.

To generate independent blocks at an identical genomic location, a construct was made comprising both blocks in a contiguous arrangement (FIG. 14). To create plants which carry the independent blocks alone, each block is excised in separate crosses using ZFNs designed to cut DNA on either side of the respective block at the corresponding ZFN binding sites (red and blue bars). FIG. 15 illustrates that the blocks are excised, generating single block inserts, after crossing with appropriate lines (*Arabidopsis* expressing ZFNs). These lines carry the PAT gene as the selectable marker. The recovery of plants with the expected phenotypes (HygR+, KanR−, PAT+, YFP+ or KanR+, HygR−, PAT+, GUS+) are confirmed via phenotype screening (herbicide resistance for the HygR, KanR and PAT genes or scorable marker gene expression of GUS and YFP) or by molecular analyses such as PCR and Southerns. Plants carrying one of the two different blocks are crossed to generate HygR+, KanR+, PAT−, GUS+, YFP+ progeny.

After molecular characterization of the resultant plants, plants with the confirmed insert are crossed with the lines that express a ZFN whose binding site is located between the two blocks using a meiotic-specific promoter to effect the exchange of DNA. This results in stacking of the two blocks together at one DNA location. The final stacked genes plants carry the HygR+, KanR+, GUS+, YFP+ configuration as a single, segregating locus. Alternatively, plants containing one of the blocks are crossed with one of the two monomers comprising the meiosis promoter/ZFN constructs, plants homozygous for the two inserts obtained and then crossed together.

Example 7.1

DNA Construction

The cloning strategies deployed for the constructions of the ZFN constructs were as essentially described in U.S. Patent Publication Nos. 2009/0111188A1 and 2010/0199389. FIG. 9 depicts an exemplary eZFN expression cassette. ZFN coding sequences were expressed using the ZmUbi1 promoter (promoter, 5' untranslated region (UTR) and intron derived from the *Zea mays* ubiquitin 1 (Ubi-1) gene; Christensen et al. (1992) *Plant Molec. Biol.* 18(4), 675-89). These were subsequently cloned into a binary GATEWAY™ destination vector containing a rice actin1 promoter driving the expression of the PAT gene. The resultant plasmids pDAB105951 (ZFN1; CL:AR), 105954 (ZFN8; RL:AR), 105952 (ZFN3; AL:PR), 105953 (ZFN6; CL:RR) designated as Block1 Excisor (eZFN1,8) or Block2 Excisor (eZFN3,6) constructs, respectively, were transferred to Agrobacterium strain DA2552recA.

The *Agrobacterium* DA2552 strain was made competent for electroporation by preparing a starter culture by inoculating DA2552 strain from a glycerol stock into 10 ml of YEP containing spectinomycin (spec) (100 μg/mL) and erythromycin (ery) (150 μg/mL). The 10 ml culture was incubated overnight at 28° C. at 200 rpm. Five milliliters of the starter culture was used to inoculate 500 ml of YEP with appropriate antibiotics in an appropriately labeled 1.5 L Erlenmeyer flask. The culture was incubated overnight at 28° C. at 200 rpm. After overnight incubation, the culture was chilled by placing it in a wet ice-water bath and swirling gently. The cells were kept at 4° C. for all further steps. The cells were pelleted by centrifuging at 4000×g for 10 min. at 4° C. in a labeled sterile centrifuge bottle in a prechilled rotor. The supernatant was poured off and discarded, then 5 to 10. mL of ice-cold sterile double-distilled water was added, and the cells were pipeted gently up and down until no clumps remained. The suspension volume was adjusted to approximately 500 ml with ice-cold sterile double-distilled water. The cells were pelleted by centrifuging at 4000×g for 10 min. at 4° C. in a prechilled rotor. The supernatant was discarded and 5 to 10 ml of ice-cold sterile double-distilled water was added; then a sterile wide-bore pipette was used to pipette the cells gently up and down until no clumps remained. The suspension volume was adjusted to approximately 250 ml with ice-cold sterile double-distilled water and the cells were pelleted again by centrifuging at 4000×g for 10 min. at 4° C. in a prechilled rotor. The supernatant was discarded and 5 to 10 ml of ice-cold sterile double-distilled water added, the pellet gently resuspended and final volume adjusted to 50 ml with ice-cold sterile double-distilled water. Cells were pelleted by centrifuging at 4000×g for 10 min. at 4° C. in a prechilled rotor. Cells were re-suspended in a final volume of 5 ml of 10% (v/v) ice-cold, sterile glycerol. Cells were dispensed into 50 µl aliquots in sterile 0.5 ml microfuge tubes and frozen in liquid nitrogen.

Twenty microliters of competent DA2552 cells were electroporated with 50 ng of plasmid DNA using a GENE PULSER® XCELL® Electroporation System (BioRad Hercules, Calif.) according to the manufacture's pre-set settings and protocols for Agrobacterium electroporation. The cells recovered for 2 hours in SOC at 28° C. and then plated on YEP spec/ery agar plates and grown for 48 h at 28° C.

Example 7.2

Exchange Locus Construct

Figure 16:
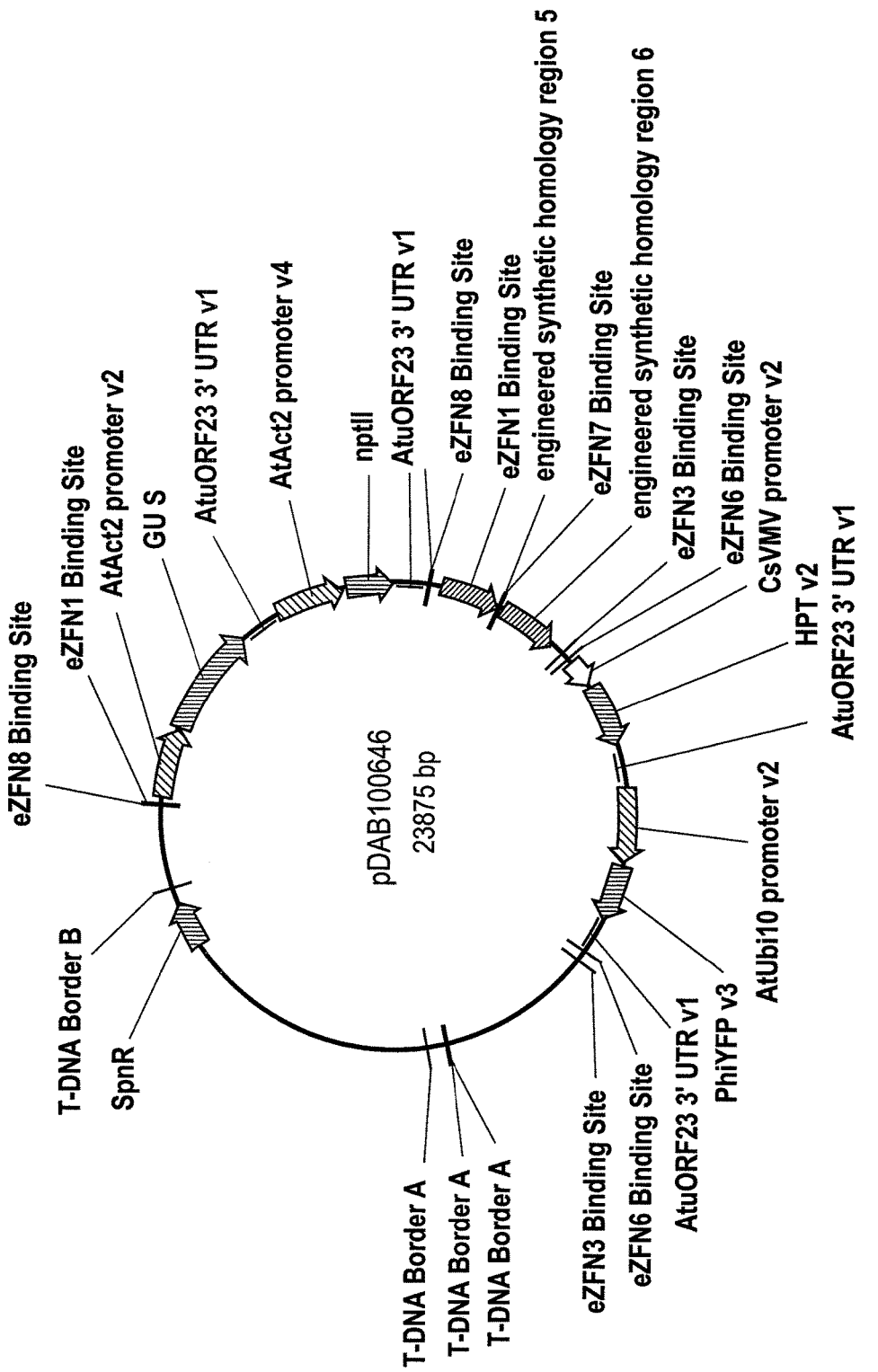
FIG. 16 is a schematic of the plasmid used for introducing the Exchange Locus into Arabidopsis. It contains Blocks 1 and 2 as described in FIG. 14 and the multiple insertion site sequence. The eZFN binding sites are indicated and flank Blocks 1 and 2 (Block1: eZFN1 and 8; Block2: eZFNs 3 and 6) or are centrally located in the multiple insertion site (eZFNs 4 and 7) to facilitate homologous recombination.

The Exchange Locus DNA construct was prepared from GATEWAY™ entry vectors including vector 1: AtAct2 promoter (AtAct2 promoter v2 (promoter, 5' untranslated region and intron from an *Arabidopsis thaliana* actin gene (ACT2); An et al. (1996) *Plant J.* 10, 107-121))/GUS (Jefferson, (1987) *EMBO J.* 6, 3901-3907)/AtuORF23 3' UTR (3' untranslated region (UTR) comprising the transcriptional terminator and polyadenylation site of open reading frame 23 (ORF23) of *Agrobacterium tumefaciens* pTi15955; Barker et al., (1983) *Plant Molec. Biol.* 2(6):335-50):: AtAct2 promoter/NPTII (Bevan et al. (1983) *Nature* 304, 184-187)/AtuORF23 3' UTR, flanked by eZFNs 1 and 8, vector 2: synthetic 2 kb region with eZFN 4 and 7 in the center of the sequence; and vector 3: CsVMV promoter/HPT (Kaster et al. (1983) *Nucleic Acids Res.* 11 (19), 6895-6911 (1983))/AtuORF23 3' UTR::AtUbi10 promoter (promoter, 5' untranslated region and intron from the *Arabidopsis thaliana* polyubiquitin 10 (UBQ10) gene; Norris et al. (1993) *Plant Molecular Biology* 21(5):895-906)/PhiYFP (Shagin et al., (2004) *Molecular Biol. Evol.* 21:841-850)/AtuORF23 3' UTR, flanked by eZFNs 3 and 6. The destination vector was prepared by inserting two 1 kb randomized synthetic DNA sequences into a Agrobacterium binary vector backbone, with restriction sites included between them to clone a GATEWAY™ ccdB negative selectable marker cassette. The entry vectors were cloned into the destination vector by an LR Clonase reaction. The resultant vector, pDAB100646 (FIG. 16) was transferred to Agrobacterium as described above.

Example 7.3

*Arabidopsis* Transformation

All transformations into *Arabidopsis* were done following the methods described by Clough & Bent (1998 *Plant J.*, 16, 735-743).

Excisor Lines

"Excisor" line constructs possess the phosphinotricin acetyltransferase (PAT) gene that conveys resistance to gluphosinate. Seven, ten and thirteen days after planting $T_1$ plants were sprayed with a 284 mg/L solution of Liberty herbicide (200 grams of active ingredient per liter (g ai/L) glufosinate, Bayer Crop Sciences, Kansas City, Mo.) at a spray volume of 10 ml/tray (703 L/ha) using a DeVilbiss compressed air spray tip to deliver an effective rate of 200 g ai/ha glufosinate per application. Survivors (plants actively growing) were identified 4-7 days after the final spraying and transplanted individually into 3-inch pots prepared with potting media (Metro Mix 360).

Expression of the eZFNs in the Excisor events is determined by reverse transcriptase PCR (RT PCR) and copy number determined by qPCR as described herein of the PAT gene and confirmed by Southern analysis. Three low copy events expressing the ZFNs at a high level are crossed to Exchange Locus events.

The Exchange Locus lines

Exchange Locus lines are generated in Arabidopsis following the methods described by Clough & Bent (1998 *Plant J.*, 16, 735-743), including selection on media containing hygromycin or kanamycin.

Example 7.4

*Arabidopsis* Crossing and Progeny Recovery

Crossing of the Exchange Locus events with the two sets of Block1 and Block2 Excisor lines are done using standard methods.

Seed from the crosses are grown on hygromycin (Block1 deletion) or kanamycin (Block2 deletion) and resistant plants analyzed for GUS expression (Block1 deletion) or YFP expression (Block2 deletion). GUS activity is determined with a histochemical assay (Jefferson et al. (1987) *Plant Mol. Biol. Rep* 5, 387-405) and YFP using fluorescent microscopy. Plants with the desired phenotypes (Block1 positive: GUS+,NPT+,HPT−,YFP−; Block2 positive: GUS−,NPT−,HPT+,YFP+) is analyzed by PCR and Southerns to confirm the desired gene configuration. Leaves from the selected plants are painted with a bialaphos-solution to assess which are PAT+.

Plants containing the Block1 and Block2 gene cassettes are crossed and progeny selected on hygromycin/kanamycin plates. HygR/KanR plants are analyzed for the presence of all genes by PCR and phenotype screening. F1 plants with the desired phenotype are grown and crossed with meiosis promoter/ZFN plants to achieve recombination between Block1 and Block2. The resultant progeny are grown on hygromycin/kanamycin plates. Plants surviving the selection are screened for GUS and YFP. Confirmation and characterization of the recombinants are done using PCR, Southerns, sequencing and segregation analyses.

Example 8

Gene Stacking at eZFN Sites

The strategies shown in FIGS. 1, 2, 4, 5 and 6 can be accomplished using the following methods.

Construct Design

Figure 4:
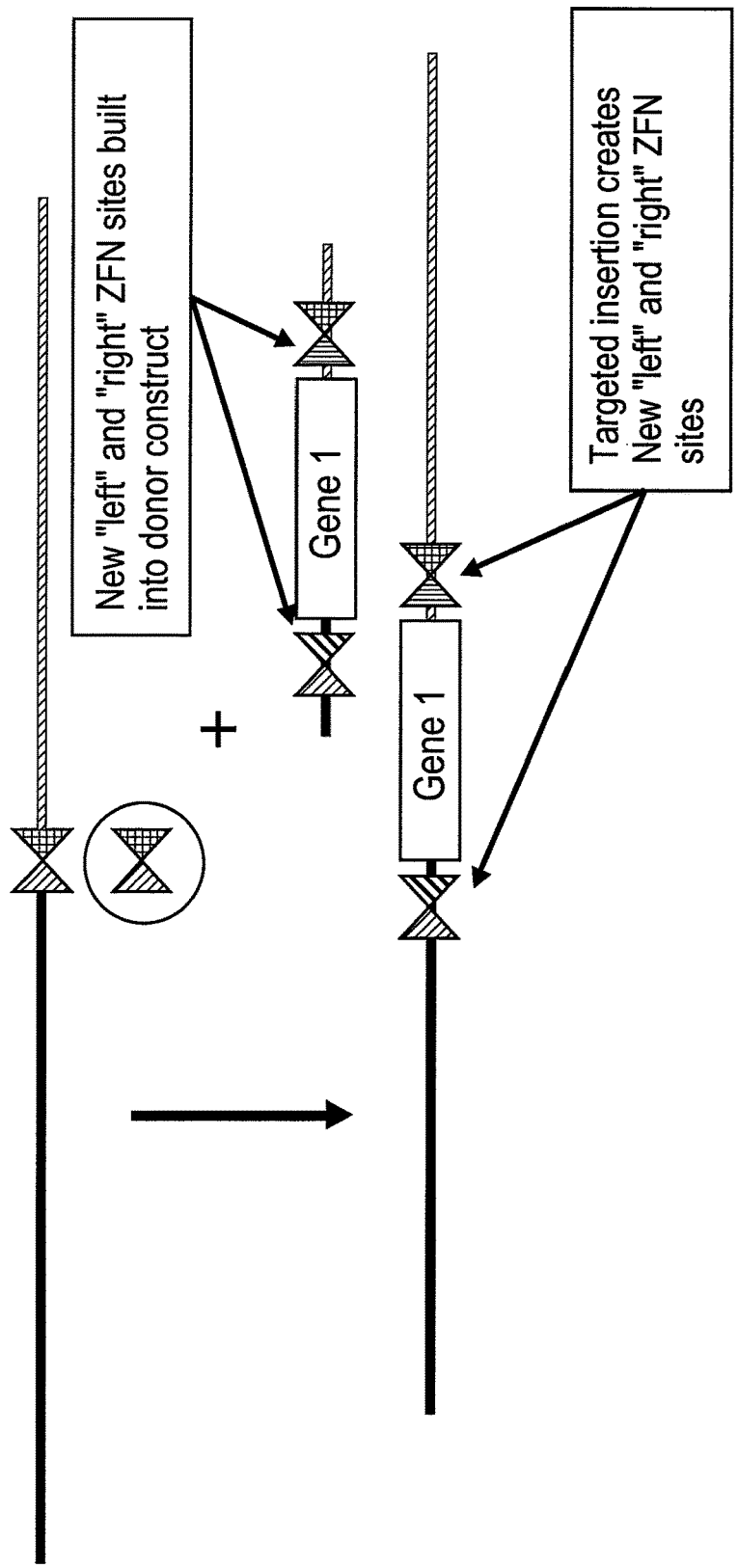
FIG. 4 is a schematic depicting the use of heterodimeric ZFN "left" and "right" target domains. The top line depicts the genome with the left and right target ZFN domains (shaded triangle and checkerboard triangle). When the appropriate ZFN pair is added in the presence of an exogenous molecule including a gene flanked by different heterodimeric pairs, the gene and flanking nuclease sites are inserted into the genome as shown.

Various combinations of heterodimeric eZFN sites can be assembled as a concatemer in a plasmid vector suitable for plant transformation. FIG. 1, FIG. 2, and FIG. 4 illustrate various versions of heterodimeric eZFN sites which can be incorporated into a vector and transformed into the chromosome of a plant.

WHISKERS™ Transformation

Embryogenic Hi-II cell cultures of maize are produced as described in U.S. Pat. No. 7,179,902, and are used as the source of living plant cells in which targeted integration is exemplified. DNA Fragments containing the heterodimeric eZFN sites linked to a plant selectable marker cassette are used to generate transgenic events. Transgenic events are isolated and characterized.

Twelve mL of packed cell volume (PCV) from a previously cryo-preserved cell line plus 28 mL of conditioned medium is subcultured into 80 mL of GN6 liquid medium (N6 medium (Chu et al., (1975) Sci Sin. 18:659-668), 2.0 mg/L 2,4-D, 30 g/L sucrose, pH 5.8) in a 500 mL Erlenmeyer flask, and placed on a shaker at 125 rpm at 28° C. This step is repeated two times using the same cell line, such that a total of 36 mL PCV is distributed across three flasks.

After 24 hours, the GN6 liquid media is removed and replaced with 72 mL GN6 S/M osmotic medium (N6 Medium, 2.0 mg/L 2,4-D, 30 g/L sucrose, 45.5 g/L sorbitol, 45.5 g/L mannitol, 100 mg/L myo-inositol, pH 6.0). The flask is incubated in the dark for 30-35 minutes at 28° C. with moderate agitation (125 rpm). During the incubation period, a 50 mg/mL (w/v) suspension of silicon carbide whiskers (Advanced Composite Materials, LLC, Greer, S.C.) is prepared by adding 8.1 mL of GN6 S/M liquid medium to 405 mg of sterile, silicon carbide whiskers. Following incubation in GN6 S/M osmotic medium, the contents of each flask are pooled into a 250 mL centrifuge bottle. After all cells in the flask settle to the bottom, content volume in excess of approximately 14 mL of GN6 S/M liquid is drawn off and collected in a sterile 1-L flask for future use. The pre-wetted suspension of whiskers is mixed at maximum speed on a vortex for 60 seconds, and then added to the centrifuge bottle.

An aliquot of 85 µg of purified DNA fragment are added to each bottle. Once DNA is added, the bottle is immediately placed in a modified Red Devil 5400 commercial paint mixer (Red Devil Equipment Co., Plymouth, Minn.), and agitated for 10 seconds. Following agitation, the cocktail of cells, media, whiskers and DNA are added to the contents of a 1-L flask along with 125 mL fresh GN6 liquid medium to reduce the osmoticant. The cells are allowed to recover on a shaker set at 125 rpm for 2 hours. 6 mL of dispersed suspension is filtered onto Whatman #4 filter paper (5.5 cm) using a glass cell collector unit connected to a house vacuum line such that 60 filters are obtained per bottle. Filters are placed onto 60×20 mm plates of GN6 solid medium (same as GN6 liquid medium except with 2.5 g/L Gelrite gelling agent) and cultured at 28° C. under dark conditions for 1 week.

Identification and Isolation of Putative Targeted Integration Transgenic Events

One week post-DNA delivery, filter papers are transferred to 60×20 mm plates of GN6 (1H) selection medium (N6 Medium, 2.0 mg/L 2,4-D, 30 g/L sucrose, 100 mg/L myo-inositol, 2.5 g/L Gelrite, pH 5.8) containing a selective agent. These selection plates are incubated at 28° C. for one week in the dark. Following 1 week of selection in the dark, the tissue is embedded onto fresh media by scraping ½ the cells from each plate into a tube containing 3.0 mL of GN6 agarose medium held at 37-38° C. (N6 medium, 2.0 mg/L 2,4-D, 30 g/L sucrose, 100 mg/L myo-inositol, 7 g/L SeaPlaque® agarose, pH 5.8, autoclaved for 10 minutes at 121° C.).

The agarose/tissue mixture is broken up with a spatula and, subsequently, 3 mL of agarose/tissue mixture is evenly poured onto the surface of a 100×25 mm dish containing GN6 (1H) medium. This process is repeated for both halves of each plate. Once all the tissue is embedded, plates are cultured at 28° C. under dark conditions for up to 10 weeks. Putatively transformed isolates that grew under these selection conditions are removed from the embedded plates and transferred to fresh selection medium in 60×20 mm plates. If sustained growth is evident after approximately 2 weeks, an event is deemed to be resistant to the applied herbicide (selective agent) and an aliquot of cells is subsequently harvested for genotype analysis. Stable plant-transformation produces single copy integrants that are used for stacking experiments.

Molecular Characterization of Events

Genomic DNA (gDNA) is extracted from isolated maize cells described and utilized as template for PCR genotyping experiments. gDNA is extracted from approximately 100-300 µl packed cell volume (PCV) of Hi-II callus that is isolated according to the manufacturer's protocols detailed in the DNEASY® 96 Plant Kit (QIAGEN Inc., Valencia, Calif.). Genomic DNA is eluted in 100 µl of kit-supplied elution buffer yielding final concentrations of 20-200 ng/µL, and subsequently analyzed via PCR-based genotyping methods.

Molecular Analysis of Copy Number

INVADER® or hydrolysis probe assays are performed to screen samples of herbicide resistant callus to identify those that contain single copy integration of the T-strand DNA. Detailed analysis is conducted using primers and probes specific to gene expression cassettes. Single copy events are identified for additional analysis.

Custom INVADER® assays are developed for the selectable marker gene analysis in Hi-II callus by Third Wave Technologies (Madison, Wis.). The genomic samples are amplified using the INVADER® assay kit and readings are collected. From these readings the fold-over zero (i.e., background) for each channel is determined for each sample by the sample raw signal divided by no template raw signal. From this data, a standard curve is constructed and the best fit determined by linear regression analysis. Using the parameters identified from this fit, the apparent selectable marker copy number is then estimated for each sample.

Selection of Transgenic Events with Target DNA

Low copy (1-2 copies of the transgene) events are screened by PCR, as described above, for an intact plant transcriptional unit (PTU) containing the selectable marker gene cassette and intact eZFN site. Copy number is further confirmed by Southern analysis using standard methods with the selectable marker gene. Callus from selected transgenic events harboring single copy, intact inserts are maintained.

Biolistic-Mediated DNA Delivery into Plant Cells Containing an eZFN

As described above, embryogenic Hi-II cell cultures of maize are produced, and are used as the source of living plant cells in which targeted integration is demonstrated. Embryogenic suspensions of maize are subcultured into GN6 liquid medium approximately 24 hours prior to experimentation as described, supra. The excess liquid medium is removed and approximately 0.4 mL PCV of cells are thinly spread in a circle 2.5 cm in diameter over the center of a 100×15 mm petri dish containing GN6 S/M media solidified with 2.5 g/L gelrite.

The cells are, cultured under dark conditions for 4 hours. To coat the biolistic particles with DNA containing a Donor DNA fragment (Block 1 in FIG. 1, Block 2 in FIG. 2, or Gene 1 in FIG. 4), 3 mg of 1.0 micron diameter gold particles were washed once with 100% ethanol, twice with sterile distilled water, and resuspended in 50 µl water in a siliconized Eppendorf tube. A total of 5 µg of plasmid DNA (containing in a single vector or in separate vectors nucleic acid molecules encoding the eZFN and Donor DNA fragment), 20 µl spermidine (0.1 M) and 50 µl calcium chloride (2.5 M) are added separately to the gold suspension and mixed on a vortex. The mixture is incubated at room temperature for 10 min, pelleted at 10,000 rpm in a benchtop microcentrifuge for 10 seconds, resuspended in 60 µl cold 100% ethanol, and 8-9 µl is distributed onto each macro-carrier.

Bombardment is performed using the Biolistic PDS-1000/HE™ system (Bio-Rad Laboratories, Hercules, Calif.). Plates containing the cells are placed on the middle shelf under conditions of 1,100 psi and 27 inches of Hg vacuum, and are bombarded following the operational manual. Sixteen hours post-bombardment, the tissue is transferred in small clumps to GN6 (1H) medium and cultured for 2-3 weeks at 28° C. under dark conditions. Transfers continue every 2-4 weeks until putative transgenic isolates resulting from integration of donor DNA begin to appear. The bialaphos-resistant colonies are generally analyzed by PCR and Southern blotting using methods detailed above for generating the isolates containing the target sequences.

Screening for Targeted Integration Events via PCR Genotyping

PCR reactions are performed to investigate the presence of an intact copy of the donor DNA. Additional reactions focus on the 5'-boundary between target and donor and the 3'-boundary between donor and target. Amplified fragments are gel-excised and purified according to standard protocols. Purified fragments are subsequently cloned into pCR2.1 plasmid using TOPO TA CLONING® Kit (with pCR2.1 vector) and ONE SHOT® TOP10 Chemically competent *E. coli* cells (Invitrogen Life Technologies, Carlsbad, Calif.) according to manufacturer's protocol.

Individual colonies are selected and confirmed to contain the amplified PCR fragment. Double-stranded sequencing reactions of plasmid clones are performed to confirm that the PCR amplified genomic sequence contains the integrated donor. Events identified to contain the donor fragment represent a target in which homology-driven repair of a ZFN-mediated double-stranded break and targeted integration of a donor DNA at a specific gene target.

Specific Application of Gene Stacking Using eZFN Sites

FIG. 1 shows variations of multiple insertion sites made up of seven (7) eZFN target sites stably transformed into the chromosome of a plant. The eZFN pairs that bind to the target sites are depicted as geometric figures. "Block 1" is an exogenous polynucleotide sequence that can be integrated into the multiple insertion site of the appropriate eZFN pair when transformed with an eZFN designed to cleave a specific eZFN site. The co-transformation of the eZFN and "Block 1" donor DNA sequence can be achieved using a biolistic transformation method, previously described above. The fidelity of the various other eZFN sites are maintained as the eZFN transformed into the plant cell does not cleave at these other sites. "Block 1" integrates into the plant chromosome via homologous recombination resulting in plant cells which contain the sequence of "Block 1." The resulting plant cells can be grown into mature plants and screened for the presence of "Block 1" using analytical molecular biology methods known in the art such as Southern Blotting, Taqman assay, or Invader assay.

FIG. 2 illustrates another variation of FIG. 1, wherein a different eZFN binding site is targeted with a polynucleotide donor sequence "Block 2." The resulting integration of the DNA fragment produces a stable plant containing "Block 2" within the chromosome.

FIG. 4 illustrates the use of eZFN "left" and "right" domains. The top line depicts the genome of a plant transformed with the left and right eZFN domains (shaded triangle and checkerboard triangle). When the appropriate eZFN is added in the presence of an exogenous molecule including "Gene 1" flanked by new and different heterodimeric eZFN sites, the "Gene 1" and flanking eZFN sites are inserted into the genome. The resulting progeny which contain "Gene 1" and flanking eZFN sites are identified and these plants can be subsequently retargeted using new heterodimeric eZFN sites that were not present within the parent plant (i.e. eZFN sites containing the shaded triangle and checkerboard triangle).

Figure 5:
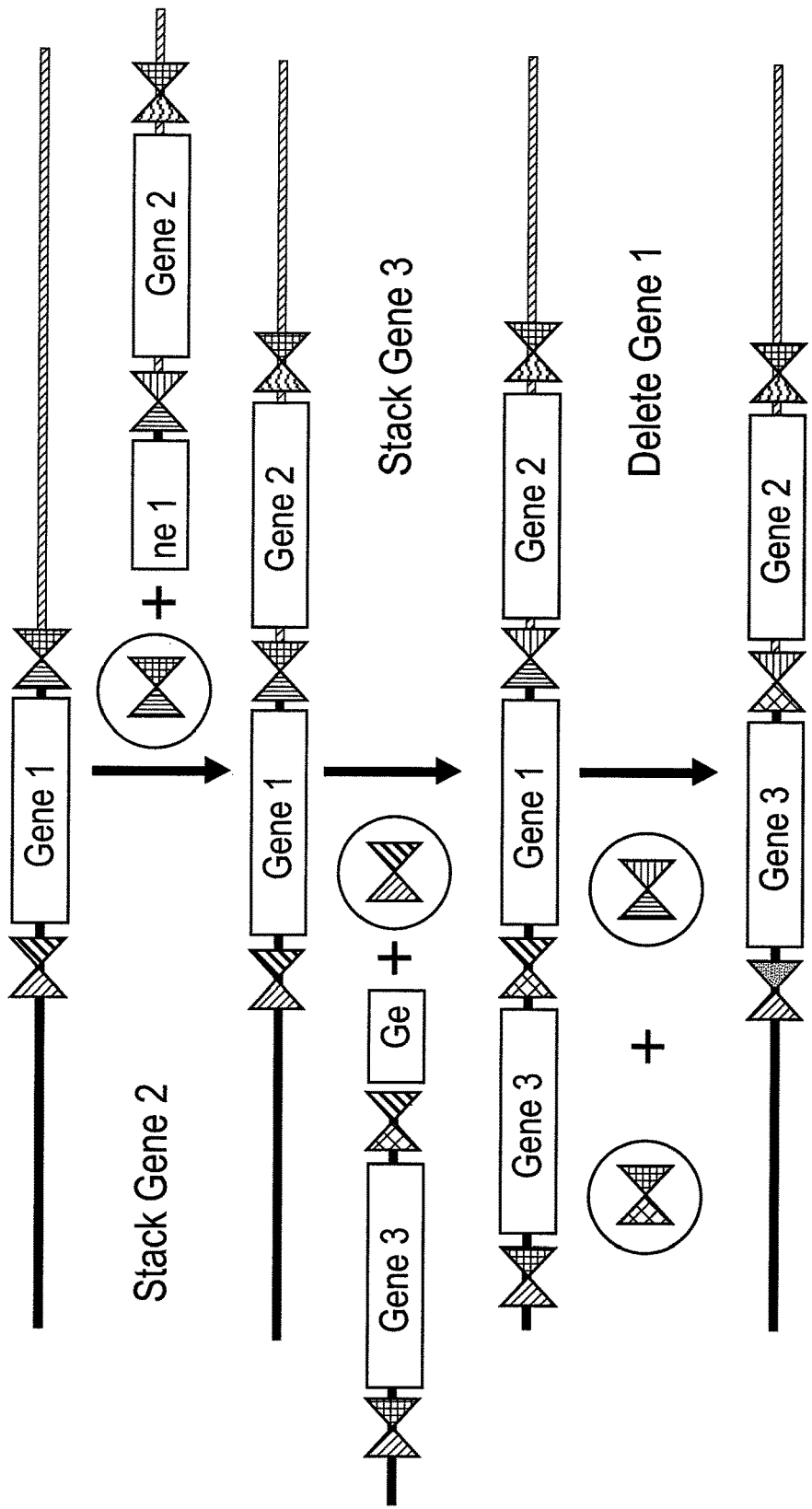
FIG. 5 is a schematic depicting integration and excision of exogenous sequences (depicted as "genes") on either side of a genomically-integrated sequence. The added genes are flanked by regions of homology to direct the gene cassettes into the appropriate site. The two halves of the ZFN target site used for insertion are re-combined by creating two new combinations in the inserted DNA. Excision of a gene cassette is accomplished by binding the appropriate ZFN pairs to cleave at the flanking ZFN target sites. Excision may require a template containing homology arms to prevent deletions of desired DNA sequence. Each "gene" can include one or more sequences, for example one or more coding sequences.

FIG. 5 and FIG. 6 illustrate how the eZFN sites can be used to stack new transgenes into a chromosomal location. Moreover, this strategy allows for the excision of other gene expression cassettes. In some instances a gene expression cassette can be completely removed (FIG. 5), in other scenarios the gene expression cassette can be removed in a specific generation of plants and eventually be reintroduced to the progeny of those plants, thereby allowing for the recycling of a gene expression cassette. A deleted marker (FIG. 6) sequence can be reintroduced via homologous recombination mediated gene targeting using the protocol described above. Gene targeting into the heterodimeric eZFN sites is completed using the protocol described above. In this example, eZFN binding sites are used to enable in planta deletion of any transgene, including selectable marker genes, from a transformed plant. See US Provisional Patent Application No. 61/297,628, filed Jan. 22, 2010, herein incorporated by reference.

All patents, patent applications and publications mentioned herein are hereby incorporated by reference, in their entireties, for all purposes.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A host cell or cell line comprising an endogenous genome and an exogenous nucleic acid molecule integrated into the endogenous genome, the exogenous nucleic acid comprising a non-coding multiple insertion site, the multiple insertion site comprising three or more different paired target sites for heterodimeric pairs of zinc finger nucleases, wherein the target sites of each paired target site are recognized by different zinc finger nucleases and further wherein (i) the target sites of each paired target site are separated from each other by 0 to 18 nucleotides; (ii) the paired target sites are separated from each other by non-coding sequences; (iii) the paired target sites are not present in the endogenous genome; and (iv) upon cleavage of one of the paired target sites by a pair of zinc finger nucleases and in the presence of a donor sequence in the host cell or cell line, the donor sequence is integrated into the genome in place of the paired target site and further wherein the donor sequence does not comprise the paired target sites cleaved by the pair of zinc finger nucleases.

2. The cell or cell line of claim 1, where one target site from each paired target site comprises the same sequence.

3. The cell or cell line of claim 1, wherein the exogenous nucleic acid molecule further comprises one or more coding sequences.

4. The cell or cell line of claim 1, wherein the cell is a eukaryotic cell.

5. The cell or cell line of claim 4, wherein the eukaryotic cell is a plant or mammalian cell.

6. A method for integrating one or more exogenous sequences into the genome of a cell, the method comprising
   (a) providing one or more pairs of zinc finger nucleases to a cell according to claim 1, wherein the zinc finger nucleases bind to a paired target site and cleave the multiple insertion site; and
   (b) contacting the cell with a donor polynucleotide comprising an exogenous sequence, wherein the exogenous sequence is integrated into the genome of the cell within the multiple insertion site and in place of the paired target site and further wherein the donor polynucleotide does not comprise the paired target sites cleaved by the pair of zinc finger nucleases.

7. The method of claim 6, further comprising repeating steps (a) and (b) with additional zinc finger nucleases that cleave additional target sites in the integrated nucleic acid molecule in the presence of additional exogenous sequences, thereby inserting the additional exogenous sequences into the genome of the cell.

8. The method of claim 6, wherein one or more of the exogenous sequences comprise one or more target sites for zinc finger nucleases.

9. The method of claim 6, wherein the target site is a zinc finger nuclease half target site, wherein, upon integration of the half target site, a target site is created.

10. The method of claim 6, wherein one or more of the exogenous sequences comprises a coding sequence and the cell expresses the product of the coding sequence.

11. A method of deleting one or more sequences inserted into the genome of a cell, the method comprising,
(a) integrating a plurality of exogenous sequences according to claim 7; and
(b) expressing the appropriate nucleases in the cell such that one or more of the exogenous sequences are deleted from the genome.

12. A method of providing a genomically altered cell, the method comprising
(a) integrating one or more exogenous sequences in at least a first cell according to the method of claim 6;
(b) allowing the first cell to develop into a sexually mature organism; and
(c) crossing the organism with a second organism comprising at least one genomic alteration to generate a second cell with at least one of the genomic alterations of the first and second organisms.

13. The method of claim 12, wherein the second cell genomic alterations comprise a plurality of heterologous genes at a single genomic location in the second cell.

14. The method of claim 12, wherein the first cell further comprises one or more deletions within the integrated nucleic acid molecule.

15. The method of claim 6, wherein the cell further comprises modifications of its genome outside the integrated nucleic acid molecule.

16. The method of claim 6, wherein the cell is a plant cell.

17. The cell of claim 5, wherein the cell is a plant cell and the paired target sites comprise sequences from a mammalian genome.

\* \* \* \* \*